(12) United States Patent
Smith

(10) Patent No.: US 8,790,666 B2
(45) Date of Patent: Jul. 29, 2014

(54) NERVE CONSTRUCT CONTAINING LIVING STRETCH-GROWN NERVOUS TISSUE

(75) Inventor: Douglas H. Smith, Boothwyn, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 2175 days.

(21) Appl. No.: 11/429,201

(22) Filed: May 5, 2006

(65) Prior Publication Data

US 2006/0292187 A1    Dec. 28, 2006

Related U.S. Application Data

(63) Continuation-in-part of application No. 10/496,476, filed as application No. PCT/US02/38670 on Dec. 4, 2002, now Pat. No. 7,429,267.

(60) Provisional application No. 60/336,975, filed on Dec. 4, 2001, provisional application No. 60/386,982, filed on Jun. 6, 2002.

(51) Int. Cl.
*A61K 9/00* (2006.01)

(52) U.S. Cl.
USPC ........... 424/400; 435/366; 435/368; 435/374; 514/8.3; 604/522; 604/93.01

(58) Field of Classification Search
CPC ..... A61K 9/0085; A61N 1/05; A61N 1/0551; A61N 1/326; A61N 1/36103; A61N 5/0601
USPC ............ 435/366, 368, 374; 424/400; 514/8.3, 514/8.4; 604/522, 93.01
See application file for complete search history.

(56) References Cited

U.S. PATENT DOCUMENTS

| | | | |
|---|---|---|---|
| 4,306,561 A | 12/1981 | De Medinaceli | 128/303.13 |
| 4,774,967 A | 10/1988 | Zanakis et al. | 128/785 |
| 4,868,913 A | 9/1989 | Tse-Kay et al. | 623/12 |
| 5,084,007 A | 1/1992 | Malin et al. | 604/20 |
| 5,834,029 A * | 11/1998 | Bellamkonda et al. | 424/570 |
| 6,264,944 B1 | 7/2001 | Smith | 424/93.7 |
| 6,365,153 B2 | 4/2002 | Smith | 424/93.7 |
| 7,429,267 B2 * | 9/2008 | Smith et al. | 607/1 |

FOREIGN PATENT DOCUMENTS

WO    WO 01/12207    2/2001

OTHER PUBLICATIONS

Smith et al. High tolerance and delayed elastic response of cultured axons to dynamic stretch injury. J Neurosci. Jun. 1, 1999;19(11):4263-9.*
Jiménez et al. Aclar discs: a versatile substrate for routine high-pressure freezing of mammalian cell monolayers. J Microsc. Mar. 2006;221(Pt 3):216-23.*
Raymon et al. Immortalized human dorsal root ganglion cells differentiate into neurons with nociceptive properties. J Neurosci. Jul. 1, 1999;19(13):5420-8.*
Galbraith et al., 1998, Cell Motil. Cytoskeleton 40:317-330.
Gimenez y Ribotta et al., 1996, Brain Res. 707:245-255.
Houle et al., 1994, J. Neural Transplant. Plast. 5:115-124.
Huang et al., 2004, J Neurosurgery 100(N4):800, Meeting Abstract for AANS Annual Meeting, Orlando, FL, May 5, 2004 "Human Dorsal Root Ganglia Neurons as Live Nerve Constructs: Implications for Tranplantation".
Huang et al., 2004, J Neurotrauma 21(N9):1297, Meeting Abstract P133, 22$^{nd}$ Annual National Neurotrauma Society Symposium, San Diego, CA, Oct. 21 & 22, 2004.
Huang et al., 2004, Meeting Abstract for AANS/CNS Annual Meeting, San Diego, CA, Mar. 19, 2004 "Human DRG Neurons as Alternative for Transplantation: A Novel Tissue-Engineered System".
Iwata et al., 2006, Tissue Engineering, 12:101-110.
Martin et al., 1996, J. Neurosci. Res. 45:588-597.
Meaney et al., 2003, Summer Bioengineering Conference, ASME, Key Biscayne FL, Jun. 2003, p. 935-936.
Pfister et al., 2003, Summer Bioengineering Conference, ASME, Key Biscayne FL, Jun. 2003, p. 131-132.
Pfister et al., 2003, Summer Bioengineering Conference, ASME, Key Biscayne FL, Jun. 2003, p. 539-540.
Pfister et al., 2004, J Neurotrauma 21(N9):1297, Meeting Abstract P98, 22$^{nd}$ Annual National Neurotrauma Society Symposium, San Diego, CA, Oct. 21 & 22, 2004.
Pfister et al., 2004, J. Neurosci. 24:7978-7983.
Pfister et al., 2005, J Neurosci Methods [Epub ahead of print Dec. 5, 2005].
Ramon-Cueto et al., 1998, J. Neurosci. 18:3803-3815.
Sato et al., 1994, Biorheology 31:143-153.
Shirinsky et al., 1989, J. Cell Biol. 109:331-339.
Smith et al, 2001, BED—vol. 50, 2001 Bioengineering Conference, ASME 2001, pp. 413-414.
Smith et al., 2001, Tissue Engineering 7:131-139, April.
Yano et al., 1997, J. Cell. Biochem. 64:505-513.

* cited by examiner

*Primary Examiner* — Gregory S Emch
(74) *Attorney, Agent, or Firm* — Saul Ewing, LLP; Kathryn Doyle

(57) ABSTRACT

The present invention relates to mechanically elongated neurons and provides useful compositions, devices and methods for treating a nerve lesion using such mechanically elongated neurons.

24 Claims, 20 Drawing Sheets

FIG. 5

| Accelerating growth rate to 8mm per day | | | | | | |
|---|---|---|---|---|---|---|
| Day | 0 | 1 | 3 | 5 | 6 | 7 |
| Axon Length (mm) | 0 | 1 | 5 | 11 | 15 | 23 |
| Displacement step (mm) | 0.002 | 0.002 | 0.002 | 0.004 | 0.004 | |
| Step interval (s) | 172 | 86.4 | 57.6 | 86.4 | 43.2 | |
| Growth Rate (mm/day) | 1 | 2 | 3 | 4 | 8 | |

| Axon stretch-growth to 5cm in length | | | | | |
|---|---|---|---|---|---|
| Day | 0 | 1 | 1.5 | 2 | 14 |
| Axon Length (mm) | 0 | 1 | 2 | 3.5 | 50.5 |
| Displacement step (mm) | | 0.002 | 0.002 | 0.002 | 0.004 |
| Step interval (s) | | 172 | 86.4 | 57.6 | 86.4 |
| Growth Rate (mm/day) | | 1 | 2 | 3 | 4 |

Gross Anatomy, 4 months

A

B

C

NERVE CONSTRUCT CONTAINING LIVING STRETCH-GROWN NERVOUS TISSUE

CROSS REFERENCE TO RELATED APPLICATIONS

This application is a continuation-in-part of U.S. application Ser. No. 10/496,476, filed Nov. 17, 2004, now U.S. Pat. No. 7,429,267 which is a National Stage application of PCT/US02/38670, filed Dec. 4, 2002, which in turn claims benefit under 35 U.S.C. §119 of U.S. provisional application Ser. Nos. 60/336,975, filed on Dec. 4, 2001, and 60/386,982, filed on Jun. 6, 2002, whose contents are incorporated herein by reference in their entireties.

STATEMENT REGARDING FEDERALLY SPONSORED RESEARCH OR DEVELOPMENT

This invention is supported in part by funds obtained from the U.S. Government (National Institutes of Health Grant Numbers AG21527, NS38104, NS048104, NS46170 and HD41699), and the U.S. Government may therefore have certain rights in the invention.

BACKGROUND OF THE INVENTION

In the United States, approximately 12,000 people each year suffer some form of spinal cord injury (SCI), with over 275,000 people chronically paralyzed from SCI. There are two general types of SCI: complete and incomplete lesions. Complete lesions leave the patient with no motor, sensory, or autonomic function below the level of the lesion. Transection of the spinal cord is the most obvious cause of a complete lesion. The level of the injury in the spinal cord determines exactly what function will be lost, as the spinal nerves that exit the cord below this are absolutely unable to transmit signals to or from the brain. Incomplete lesions can take a variety of forms, and depending on the nature of the trauma, a range of motor and sensory abilities may be present.

Non-traumatic pathologies such as stroke and Parkinson's disease are also often characterized by a patient's inability to successfully translate a desire into the appropriate motions of the relevant limbs. Central nervous system pathologies are often responsible for varying levels of paralysis, which cause immense suffering in the affected population.

The capacity for adult mammalian neurons to regenerate and restore functionality following injury is very limited in the central nervous system (CNS) (Fournier et al., 2001, Curr. Opin. Neurobiol. 11:89-94; Davies et al., 1997, Nature 390: 680-683; Qiu et al., 2000, Glia. 29:166-174). Major emphasis has been placed on transplantation of fetal neural tissue or cells as a potential strategy to ameliorate functional deficits and to enhance axons to regenerate in the CNS. In addition, transplantation of fetal tissue has resulted in some functional recovery in neurodegenerative diseases, such as Parkinson's and Huntington's disease (Bjorklund et al., 2000, Nat. Neurosci. 3:537-544). However, clinical use of fetal cells is limited by the availability of donor tissue as well as logistic, immunological, and ethical concerns (Hoffer et al., 1991, Trends Neurosci. 14:384-388; Widner et al., 1988, Brain Res. 472:287-324). Accordingly, there has been enormous attention on finding an alternative source of neurons that are suitable for transplantation and repair. In particular, extensive effort has been placed on neural stem cells as a source of multipotent graft tissue. However, neural stem cells primarily differentiate into glia when transplanted into normeurogenic regions of adult brain or spinal cord (Cao et al., 2001, Exp. Neurol. 167:48-58; Chow et al., 2000, Brain Res. 874:87-106; Fricker et al., 1999, J. Neurosci. 19:5990-6005; Gage et al., 1995, Proc. Natl. Acad. Sci. USA 92:11879-11883; Herrera et al., 1999, Ann. Neurol. 46:867-877; Shihabuddin et al., 2000, J. Neurosci. 20:8727-8735).

Methods for transplantation of neural tissue into the area of an SCI, in order to reduce the deficits associated with the injury and to promote functional recovery, are currently under development. In animal studies, embryonic tissue transplants into the areas of a lesioned spinal cord have been shown to survive and to reinnervate certain regions of the spinal cord (Bjorklund et al., 1986, Neurosci. 18:685-698; Buchanan et al., 1986, Brain Res. 381:225-236; Moorman et al., 1990, Brain Res. 508:194-198; Ribotta et al., 1996, Brain Res. 707:245-255). Such studies have shown that the time of transplant after injury the type of cell transplanted affects the success of the attempted transplant. These transplant studies have focused on reinstating nerve fiber connections using ex vivo donor material or attempting to grow long nerve fibers by attractant molecules. However, neither approach to transplantation has achieved success in growing nerve fibers over a distance of more than a few millimeters.

Other methods attempted as a way to bridge or fill spinal cord injury lesions that include transplanting peripheral nerves, transplanting progenitor cells, transplanting stem cells, or transplanting dissociated cells from nervous tissue (McDonald, 1999, Sci. Amer. 281:64-73; Zompa et al., 1997, J. Neurotrauma 14:479-506). Some of these attempts have resulted in improved functional outcome in animal models of spinal cord injury. However, improved function has not been attributed directly to the reinstatement of spinal cord signals through the transplant. Rather, it has been proposed that the primary benefit of the transplanted tissue in these models is through physical and biochemical support for the host tissue surrounding the lesion (Stichel et al., 1998, Prog. Neurobiol. 56:119-148; Anderson et al., 1995, Brain Pathol. 5:451-457). While the results of these studies have been promising, the goal of re-establishing an axonal connection through a spinal cord lesion has yet to be realized.

Another neural injury is amputation of a digit or limb. Historically, such injuries have been treated by providing a prosthesis. Despite remarkable improvements in the engineering of such prostheses, however, they remain relative cumbersome with limited function. Current prosthetic devices do not replace sensory systems and cannot adapt movements based on sensory feedback as a natural limb functions. In recent years, the concept of neurally-controlled prostheses has become the focus of much research. The strategy is to use regions of the undamaged nervous system to provide command signals to drive prosthetic functions. The most vigorously-pursued approach attempts to harness external recordings obtained from the motor cortex. These non-invasive techniques obtain the user's intent from scalp-derived sensorimotor rhythms, typically those of the mu or beta frequency bands. Studies in rats, non-human primates, and quadriplegic patients have shown that upon sufficient training, the user can learn to move a cursor in two-dimensional space by manipulating these frequencies (Wolpaw et al., 2004, Proc. Natl. Aca. Sci. 101: 17849-17854). While the risk of surgery is avoided in this approach, a sophisticated system requiring several degrees of freedom has not yet been realized.

More invasive techniques have also been developed. These techniques chronically implant micro-electrodes into the primary motor cortex or spinal cord to local record neuronal activity. Neuronal population decoding algorithms are used to decipher the recorded signals in real-time (Kennedy et al., 2004, IEEE Trans. Neural Syst. Rehabil. Eng. 12:339-344). This method, however, involves complex computations, and significant clinical risks arise from the chronic implantation of electrodes. Moreover, findings from functional magnetic resonance imaging studies indicate that there is extensive overlap of the cortical representations of different limb regions, adding additional difficulty to implant positioning and signal decoding (Rao et al., 1995, Neurology 45:919-924).

There remains, therefore, a need in the art for a composition and method of treatment for nerve lesions, such as spinal cord injuries. The invention addresses and meets these needs.

SUMMARY OF THE INVENTION

The present invention provides a composition comprising at least one mechanically elongated neuron, and a biocompatible matrix. In an embodiment, a mechanically elongated neuron is synapsed.

The invention further provides a method of treating a nerve lesion in a subject, the method comprising the step of administering to the subject a therapeutically effective amount of the composition. In an embodiment, the at least one mechanically elongated neuron of the composition is synapsed prior to the administering step. In another embodiment, the nerve lesion is in the central nervous system of the subject. In an embodiment, the nerve lesion is a spinal cord injury. In an embodiment, the subject is a human.

In an embodiment of the inventive composition or the method using the composition, the at least one mechanically elongated neuron is a dorsal root ganglion (DRG) neuron, a cortical neuron or a sympathetic ganglion neuron. In an embodiment, the neuron is human. In an embodiment, an axon of the at least one mechanically elongated neuron is elongated to at least about 1 centimeter. In another embodiment, the axon is elongated to at least about 5 centimeters.

In an embodiment of the inventive composition or the method using the composition, the biocompatible matrix comprises a collagen hydrogel. In an embodiment, the biocompatible matrix further comprises one or more neurotrophic factors. In an embodiment, the one or more neurotrophic factors is selected from the group consisting of: nerve growth factor (NGF), brain derived neurotrophic factor (BDNF), neurotrophin 3 (NT-3), neurotrophin 4/5 (NT-4/5), neurotrophin 6 (NT-6), neurotrophin 7 (NT-7), ciliary neurotrophic factor (CNTF), neurturin (NTN), persephin, artemin, basic fibroblastic growth factor (bFGF), glial-cell-derived neurotrophic factor (GDNF), purpurin and a synthetic neurotrophin. In certain embodiments, the one or more neurotrophic factor is nerve growth factor.

In an embodiment of the inventive composition or the method using the composition, the composition further comprises a sheath, wherein the sheath at least partially enfolds said composition.

The invention also provides a device comprising integrated neuronal cells interfaced with an electronic device, wherein the neuronal cells are human cells.

In an embodiment of the inventive device, the neuronal cells are human DRG neuronal cells. In an embodiment of the inventive device, the neuronal cells are elongated using a mechanical device. In an embodiment, the neuronal cells are elongated to at least about 1 cm. In another embodiment of the inventive device, a first neuronal cell is on the electronic device and a second neuronal cell is on a membrane and the first and second neuronal cells are synaptically integrated.

The invention further provides a method for controlling the function of a prosthesis, the method comprising the steps of implanting the second neuronal cell of the inventive device in direct contact with a peripheral nerve in a subject having a prosthesis; allowing the second neuronal cell to synaptically integrate with the peripheral nerve; interfacing the electronic device with the prosthesis, and training the subject to control the function of the prosthesis.

In an embodiment of the method for controlling the function of a prosthesis, the training step comprises operant conditioning. In an embodiment, the electronic device is a multi-electrode array. In an embodiment, the subject is a human. In an embodiment, the neuronal cells are human cells. In an embodiment, the neuronal cells are obtained from the subject.

In an embodiment of the method for controlling the function of a prosthesis, the method further comprises the step of connecting a sensor transducer on the prosthesis to the electronic device to provide an electrical signal back to the electronic device. In an embodiment, the sensor transducer detects a physical parameter selected from the group consisting of: temperature, pressure, force amplitude, force direction, force amplitude and direction, torque, light and vibration.

These and other aspects of the present invention are set forth in more detail in the following description of the invention.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2, comprising

FIG. 5 is a flowchart detailing two individual on stretch-growth paradigms. Top: scheme to reach an axon growth rate of 8 mm/day. Bottom: scheme to produce 5 cm long axon tracts.

FIG. 6, comprising FIG. 6A, top image, illustrates a neuro-electrode interface of the invention surgically transplanted to connect with a peripheral nerve stump in an affected limb. The elongated neurons are shown inside a cylindrical sheath. The electrode array is at the right end of the image. FIG. 6A, bottom image, illustrates three modes of axon integration that may occur after transplantation: 1) sprouting axons from the host proximal nerve stump grow into the nerve construct and synapse on transplanted neurons (small arrow above nerve construct); 2) grow through the nerve construct (large arrow below nerve construct); and 3) axons from the transplant grow out proximally into the host nerve and spinal cord (shown as thin black lines within nerve stump). FIG. 6B illustrates (i) a nerve construct comprising elongated neurons embedded in a matrix and inserted into a sheath, being transplanted into a site of nerve lesion, having a proximal and a distal nerve stump. (ii) After transplantation, axons from the construct grow out both proximally and distally into the host nerve (small arrows). (iii) The construct serves as a living labeled pathway to guide sprouting axons from the host proximal nerve stump across extensive nerve damage (large arrow) to reinervate tissue distal to the lesion.

FIG. 9, comprising FIG. 9A is an electron microscopy image of a small fascicle comprised of stretch-grown axons approximately 100-250 nm in diameter. Scale bar=10 μm. Square box is depicted enlarged in FIG. 9B. FIG. 9B is an electron microscopy image of a small fascicle comprised of stretch-grown axons approximately 100-250 nm in diameter. Scale bar=1 μm. FIG. 9C is an image of a transmission electron micrograph of a cross section near the center of axon fascicles in not-stretch conditions. Scale bar=500 nm. FIG. 9D is an image of a transmission electron micrograph of a cross section near the center of axon fascicles in axons stretched to a length of 5 cm in 14 days. Scale bar=500 nm.

FIG. 10, comprising FIG. 10A—CGRP; FIG. 10B—RMO-254; FIG. 10C—SMI-31; FIG. 10D—NF 200).

FIG. 11, comprising FIG. 10A depicts representative sodium and potassium currents recorded while the holding potential was stepped up in 10 mV increments from −70 mV to +90 mV. FIG. 10B depicts the current-voltage relationship of human DRG neurons in culture, generated by analysis of peak sodium and potassium currents.

FIGS. 13A, 13B, 13C, 13D, 13E and 13F, is a series of schematic drawings of the open-door expansive laminoplasty and transplant of nerve construct transplantation procedure. FIGS. 13A, B and F illustrate the laminoplasty of a rat spine with a 10 mm lateral hemisection. FIG. 13C is an illustration of the DRG nerve construct after being encased in a hydrogel. FIG. 13D depicts the hydrogel-encased nerve construct rolled into a cylindrical shape with a micro-spatula. FIG. 13E depicts the DRG nerve construct transplanted into the cavity. FIG. 13F depicts the injured spinal cord after the nerve construct transplant and closure of the laminae.

FIGS. 14A and 14B, are images of immunostained nervous tissue one month after DRG nerve constructs were transplanted into an injured spinal cord. FIG. 14A is two images of transplanted neurons and axons visualized by labeling with anti-BDA, anti-CGRP, and anti-NF200 antibodies. FIG. 14B is six images depicting Triple labeling with anti-CGRP, anti-NF200 antibodies, and Cell Tracker. Scale bars, 20 μm.

FIGS. 15A and 15B, is a series of images of transplanted neurons under confocal fluorescent microscopy. FIG. 15A is series of images of neurons visualized by labeling with anti-CGRP, anti-SMI 31 &32 antibodies, and Cell Tracker. FIG. 15B is a series of images of neurons visualized with anti-CGRP and anti-synaptophysin antibodies. Synaptophysin is a synaptic marker. Scale bars, 20 μm.

FIGS. 16A, 16B, 16C and 16D, is a series of images of representative injured nerve sites four months after transplantation. FIG. 16A depicts a site that received no repair. FIG. 16B shows a site that received a reverse autograft. FIG. 16C shows a site that received a nerve construct of the invention. FIG. 16D shows a sham injured site.

FIGS. 17A, 17B and 17C, depicts an image (17A) of stimulating and recording electrodes on either side of a lesion site after repair, and representative action potential tracings for a repaired (17B) and non-repaired nerves (17C).

FIGS. 18A, 18B, 18C and 18D, is a series of images of fluorescent micrographs of immunostained rat DRG neurons 4 months post-transplant (18A) H&E stain; (18B) NF200 immunoreactivity; (18C) CGRP immunoreactivity specific for DRGs; and (18D) merged NF200 and CGRP stains.

FIGS. 20A, 20B and 20C, is a series of images of a section of a transplanted injury region. FIG. 20A depicts the GFP+ DRG neurons and axons. FIG. 20B shows the AP+ host axons in the same image intertwined with the transplanted cells. FIG. 20C merges the two images.

DETAILED DESCRIPTION OF THE INVENTION

Figure 1:
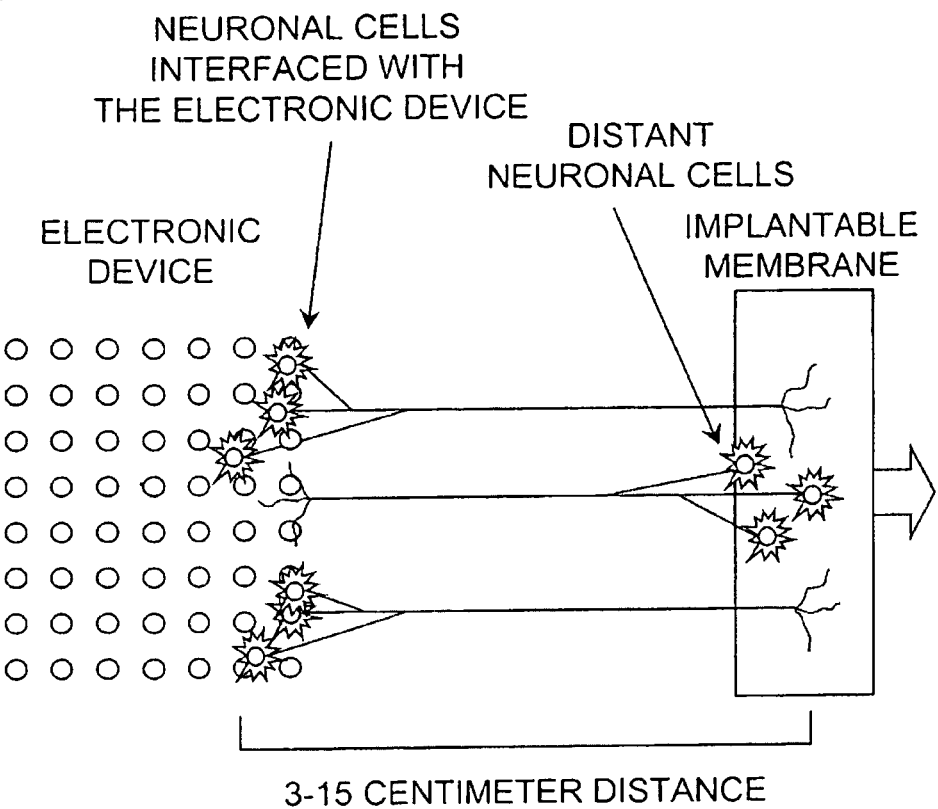
FIG. 1 is a schematic representation of integrated elongated neuronal cells attached to an implantable membrane and an electronic device.

The invention is a composition and a method of using it, and a device and a method of making the device. The composition and the device each comprise at least one neuronal cell, preferably an elongated neuronal cell. A method of using the composition to treat a nerve defect is also provided.

This application is a continuation-in-part of U.S. application Ser. No. 10/496,476, filed Nov. 17, 2004, the disclosure of which is incorporated herein by reference in its entirety.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent based on the context in which it is used.

As used herein, "in vitro" and "ex vivo" are used interchangeably to refer to conditions outside the body of a living organism. Thus, in vitro culturing and ex vivo culturing both refer to culturing outside the body of a living organism.

As used herein, a "nerve construct" refers to composition comprising at least one mechanically elongated neuron and a biocompatible matrix. The at least one mechanically elongated neuron possesses an elongated axon that spans a distance and is connected to another cell, preferably another neuron and more preferably, another mechanically elongated neuron. The biocompatible matrix in the composition provides physical support for the at least one mechanically elongated neuron, particularly for the at least one elongated axon.

As used herein, a "mechanically elongated neuron" refers to a neuron that has an increased length as a result of an ex vivo stretching procedure compared to a comparable neuron that has not been subjected to the ex vivo stretching procedure. A mechanically elongated neuron comprises a cell body and at least one elongated axon. Exemplary stretching procedures are described herein and in U.S. Pat. No. 6,365,153. "Mechanically elongated neuron" and "stretch-grown neuron" are used interchangeably herein.

As used herein, "biocompatible" refers to a material that is substantially non-toxic to neuronal cell bodies and axons and that is substantially non-toxic to the cells and tissues of a recipient of the composition. A biocompatible material, when introduced into an individual, is not toxic or injurious to that individual, nor does it induce immunological rejection of the material in the mammal.

As used herein, a "matrix" refers to a material which may be used to embed or coat mechanically elongated neurons, or the elongated axons thereof, and which provides physical support. As such, the physical form of the matrix is a highly viscous liquid, a semi-solid or a solid. While the matrix may comprise a liquid growth medium, such a liquid growth medium, alone, cannot serve as a matrix as used herein. The matrix enables the elongated axons to be handled readily, for instance, for transplantation to the site of a nerve lesion, while both maintaining the integrity of the mechanically elongated neurons and also providing a permissive environment for subsequent nerve regeneration.

As used herein, "biodegradable" refers to the capacity of a substance to be physically and/or chemically broken down by an living organism.

As used herein, "synapse" refers to a junction between a neuron and another cell, across which chemical communication flows.

As used herein, "synapsed" refers to a neuron that has formed one or more synapses with one or more cells, such as another neuron or a muscle cell.

As used herein, "synaptically integrate" refers to the formation of at least one synapse between a neuronal cell and at least one other cell. The other cell may be a nerve cell, a muscle cell or another neuronal cell target. For instance, two neuronal cells are synaptically integrated if at least one synapse exists between the two cells.

As used herein, a "sheath" refers to a structure intended to support, position and/or hold a nerve construct in place, for instance, in a nerve lesion site. A sheath at least partially enfolds a nerve construct. As used herein, "at least partially enfolds" encompasses partial or complete surrounding of part or all of a nerve construct. It therefore encompasses a completely surrounded nerve construct. Surrounding a nerve construct means the at least one mechanically elongated neuron, embedded in or coated with the biocompatible matrix, is surrounded by a sheath. While any structure may be used, preferably the sheath is a sheet or film that is manipulated to surround part or substantially all of a nerve construct. "Sheath" as used herein does not refer to the myelin sheath, which is found on the axons of some neurons.

As used herein, a "neurotrophic factor" is a biological molecule that contributes to the growth and survival of neurons during development, and/or for maintaining adult neurons.

As used herein, a "therapeutic treatment" is a treatment administered to a subject for the purpose of diminishing or eliminating one or more symptoms of a disease, defect, disorder or condition.

As used herein, "treating a nerve lesion" means reducing the frequency and/or the severity of a symptom of the nerve lesion.

As used herein, a "therapeutically effective amount" is the amount of a composition of the invention sufficient to provide a beneficial effect to the individual to whom the composition is administered.

As used herein, "sensor transducer" refers to a device that receives a signal or stimulus as an input energy of one form and converts it to output energy of another form. The signal or stimulus may be any physical parameter, including, but not limited to, temperature, pressure, force such an amplitude and/or direction, torque, light, vibration. The conversion to an output energy encompasses direct or indirect proportionalities, linear or non-linear proportionalities and also encompasses the notion of a threshold for signal generation thresholds above a signal is generated.

As used herein, "operant conditioning" refers to a positive feedback training, where a subject can learn to induce distinct electrical signals from a nerve to drive a device. Synonyms known to the skilled artisan include "instrumental conditioning" and "instrumental learning".

DESCRIPTION

The primary functional constituents of the spinal cord are myelinated axons and neurons. Signals travel from brain to body and back via these axons which synapse to spinal neurons communicating with the targeted body region. At present, electronic devices to interface with this complex system of communication include wires or devices placed in proximity with the region of the brain of interest. However, only very crude signals can be recorded from or transferred to the brain in this fashion.

An improved device has now been found to bridge electronic devices with biological processes. The device is integrated neuronal cells physically attached to or grown onto an implantable membrane and an electronic device (FIG. 1). The electronic device is used to send signals to or receive signals from the brain and/or other peripheral regions of the body. The advantage of the current device is that it comprises a living, spontaneously adaptive system of neuronal cells and an electronic device. Furthermore, when the neuronal cells have been mechanically elongated they allow for the electronic device to be located either outside of the body or implanted at an internal location which can be tolerated by the patient.

One aspect of the invention provides a method of producing integrated neuronal cells interfaced with an electronic device. The method comprises placing a first population of neuronal cells on an electronic device which is adjacent to a membrane containing a second population of neuronal cells. The membrane may be any material, however a biologically absorbable material is preferable as it is more compatible for transplantation into tissue. The two populations of neurons are allowed to mature and integrate among each other, including growth of axons across the border between the electronic device and membrane. In a preferred embodiment, the electronic device and membrane are progressively separated using, for example, a micro-stepper motor system (FIGS. 3 and 4; see, e.g., U.S. Pat. No. 6,264,944, herein incorporated in its entirety), resulting in two populations of cell bodies connected together by elongated fasicular axon tracts. In one embodiment, the membrane containing the second population of neuronal cells is implanted in or near a nerve in the peripheral nervous system.

In embodiments where the electronic device is interfaced with a nerve bundle, a signal may be transmitted from an external control module to stimulate one, some, or all of the axons in the nerve bundle, thereby causing, for example, contraction of a muscle. Preferably, the control module contains circuitry which regulates the magnitude, frequency, and/or duration of the electric signal transmitted by the electronic device.

In another preferred embodiment, the electronic device interfaced with a neuronal cell or nerve bundle comprises a multi-electrode array, as exemplified herein, or any electronic device capable of transmitting and receiving electrical signals including, but not limited to, an electrode, microchip or sensor/actuator.

In another aspect of the invention, a nerve construct is provided. A nerve construct comprises at least one mechanically elongated neuron and a biocompatible matrix. As a result of the elongation procedure, described elsewhere herein, the at least one mechanically elongated neuron is synapsed to another cell, preferably a neuron, by means of at least one elongated axon spanning the distance between the two cells. Preferably, the nerve construct comprises two physically-separate populations of cell bodies of mechanically elongated neurons that are connected to each other by at least one elongated axon, and preferably, by bundles of elongated axons emanating from both populations of cell bodies. The nerve construct can be used alone or can be part of the device of the invention.

In the nerve construct, the biocompatible matrix supports the at least one mechanically elongated neuron, and in particular, the at least one elongated axon. The support provided by the matrix enables the at least one mechanically elongated neuron to be handled and manipulated more readily and with a reduced risk of disrupting synapse and/or axon integrity. The biocompatible matrix must therefore have sufficient stiffness to support the elongated axons, while providing flexibility to permit to flex or bend the nerve construct as necessary. The biocompatible matrix preferably provides a permissive environment for nerve regeneration. Non-limiting examples of materials useful as a biocompatible matrix in the instant invention include: collagen, self-assembling peptides (e.g. U.S. patent application publication number 200450287186), alginate, agarose, fibrin, hyaluronic acid, chitosan, poly (HEMA-MMA), polylactic acid (PLA), other natural and synthetic polymers, and combinations thereof. The biocompatible matrix is, optionally, biodegradable. In a preferred embodiment, the biocompatible matrix is a hydrogel. In another preferred embodiment, the biocompatible matrix is a hydrogel comprising collagen. In another preferred embodiment, the biocompatible matrix comprises 80% collagen-hydrogel.

The biocompatible matrix, optionally, comprises one or more compounds that contribute directly or indirectly to the regeneration of neural tissue. This is particularly useful when a nerve construct is used the therapeutic method of the invention. Such compounds include, but are not limited to, neurotrophic factors, nutrients, and compounds that counteract compounds that inhibit growth and regeneration of neural tissue. Such compounds may be proteins, peptides, lipids, nucleic acids, e.g. RNA, siRNA or DNA, small molecules, and carbohydrates. Optionally, the compound is covalently attached to the biocompatible matrix.

Neurotrophic factors are substances responsible for the growth and survival of neurons during development, and for maintaining adult neurons. Non-limiting examples of neurotrophic factors useful in the instant invention include: nerve growth factor (NGF), brain derived neurotrophic factor (BDNF), neurotrophin 3 (NT-3), neurotrophin 4/5 (NT-4/5), neurotrophin 6 (NT-6), neurotrophin 7 (NT-7), ciliary neurotrophic factor (CNTF), neurturin (NTN), persephin, artemin, basic fibroblastic growth factor (bFGF), glial-cell-derived neurotrophic factor (GDNF), purpurin and synthetic neurotrophins, such as pan-neurotrophin-1 (PNT-1). In one embodiment, the matrix comprises NGF. Compounds that counteract compounds that inhibit growth and regeneration of neural tissue include, but are not limited to, antibodies against compounds such as myelin-associated glycoprotein and oligodendrite myelin glycoprotein. In a preferred embodiment, the biocompatible matrix comprises NGF. In another preferred embodiment, the biocompatible matrix is a hydrogel comprising collagen and further comprising NGF.

The nerve construct may further comprise a biocompatible sheath. The sheath is intended to provide additional physical support to the nerve construct. The sheath may also provide a means of securing the position of a nerve construct at the site of a nerve lesion. The sheath partially or wholly enfolds or surrounds at least part of the nerve construct. For instance, in one embodiment, the sheath is a sheet of bioresorbable material which forms a cylinder around substantially all of the elongated fasicular axon tracts that are coated or embedded in the biocompatible matrix. In another embodiment, the sheath forms a cylinder around substantially the entire length of the nerve construct. In another embodiment, the sheath is a partial cylinder, that is the sheath does not form a complete circle, and it enfolds substantially the entire length of the elongated fasicular axon tracts. Preferably, the sheath is flexible and can be sutured. Optionally, the sheath is bio-resorbable and/or biodegradable. Non-limiting examples of materials useful as a sheath include: surgical meshes, collagen-based sheets, nylon membranes and expanded PTFE membranes.

In one embodiment, the nerve construct is constructed by mechanically elongating neurons, as described elsewhere herein, and then coating, embedding and/or encasing the elongated neurons, including the elongated fasicular axon tracts, in the biocompatible matrix. In one aspect, the elongated neurons are encased in a biocompatible matrix immediately after completion of the elongation process. In another aspect, the biocompatible matrix is present during the elongation process. In another aspect, the elongated neurons are encase immediately prior to transplantation. In another aspect, the nerve construct is essentially surrounded by a sheet of a biocompatible material to form a sheath. Such a composition may be prepared, for instance, by placing a sheet of biocompatible material on the bottom of the elongator apparatus and stretch-growing axons over it. The stretch-grown neurons may then be coated with the biocompatible matrix prior to removal from the elongator frame, and the sheet of biocompatible material, with the elongated neurons and biocompatible matrix, are removed from the elongator frame. The elongated neurons and matrix are then surrounded by the sheet of biocompatible material, for instance, by bringing two edges of the sheet together to form a cylinder, thus forming a sheath. The skilled artisan, armed with the instant disclosure, will recognize other methods of assembling the nerve construct composition of the invention.

Exemplary stretch-growth paradigms for embryonic dorsal root ganglion are shown in FIG. 5. In one aspect, in the first 24 hours of stretch growth, the optimal stretch parameter for net elongation of 1 mm/d is 2 μm displacements every 172 seconds. After the first 24 hours, axons tolerate progressively greater rates of elongation as long as sufficient acclimation time is allowed between increases in the net rate. In another aspect of stretch growth, using human adult dorsal root ganglion, axons are pretensioned, e.g. 0.25 mm/day, for a day prior to elongation. Non-limiting examples of net elongation rates for human adult dorsal root ganglion after pretensioning include 0.5 mm/day and 1 mm/day. Guided by the instant disclosure, the skilled artisan is able to optimize stretch-growth conditions.

In a preferred embodiment of the present invention, neuronal cells are derived from any cell that is a neuronal cell (e.g., cortical neurons, dorsal root ganglion neurons or sympathetic ganglion neurons) or is capable of differentiating into a neuronal cell (e.g., stem cell) and can function in the central nervous system or peripheral nervous system. Preferably, the neuronal cells are dorsal root ganglion neurons or sympathetic ganglion neurons, more preferably, human dorsal root ganglion neurons or human ganglion sympathetic neurons. In one embodiment, the elongated neurons are elongated to at least about 1 centimeter. In another embodiment, the elongated neurons are elongated to at least about 5 centimeters. Neuronal cells useful in the invention may be derived from cell lines or other mammalian sources, such as donors or volunteers. Preferably, the neuronal cell is from a human. In one embodiment, the neuronal cells are human dorsal root ganglion neurons obtained from a cadaver. In another embodiment, the neuronal cells are human dorsal root ganglion neurons obtained from patients who have undergone ganglionectomies. Alternatively, sympathetic ganglion neurons are obtained from a cadaver or through endoscopic extraction from a subject. Furthermore, the neuronal cells may be singular, integrated neuronal cells or a plurality of integrated neuronal cells (i.e., an integrated nerve bundle). Optionally, the neuronal cell is genetically modified. For instance, neuronal cells may be modified to express transiently a neurotrophic factor. Methods of genetically modifying neuronal cells, such as photoporation and viral transfection, are well known to the skilled artisan.

It is contemplated that the nerve construct and the device of the invention will be useful as a source of transplant material for patients with spinal cord injury as well as other nerve lesions, such as those derived from a neurodegenerative disease, including Parkinson's disease. The composition and device of the invention may also be used to restore communications of a severed limb or organ of the peripheral nervous system with the central nervous system.

Nerve lesions that may be treated using a nerve construct of the invention include lesions in the central nervous system (CNS) and/or in the peripheral nervous system (PNS). The CNS includes the brain, spinal cord, optic, olfactory and auditory systems. The PNS includes neurons and nervous tissue that reside or extend outside of the CNS. In one embodiment, the lesion is a spinal cord injury. In another embodiment, the lesion is an optic nerve lesion. In another embodiment, the lesion is any peripheral nerve lesion, including upper and lower limb and genitourinary nerve damage.

Methods for transplantation of the cells of the device of the invention are well known to those of skill in the art of cell transplantation. Suitable transplant material may be evaluated by using well-known electrophysiological and fluorescence techniques to demonstrate that digital signals can be sent from the electronic device to the attached neurons and stimulate an action potential to be received by the distant neurons. Likewise, distant neurons grown on the transplantable membrane may be stimulated to demonstrate that a signal can be received by the electronic device.

Transplanted cells of the device are oriented such that the distant neuron is implanted in the brain at or near a site of nerve damage, and the electronic device is exteriorized. Preferably, the cells of the device are transplanted at or near a peripheral nerve. See FIG. 6A. In this manner, the signals generated by the brain cells or viable cells at or near the site of nerve damage may be exteriorized. Signals received from the brain, for example, may be used to control external prostheses, such as an assist robot or an artificial arm; computers or computer displays; or functional electrical stimulation of muscles of paralyzed individuals for the restoration or enhancement of movement.

As one of skill in the art can appreciate, the device of the present invention would permit a signal to be sent from the brain to the electronic device to allow a subject to control the function of a device such as a prosthesis or robot. That is, the subject would transmit a signal; the impulse would be transmitted by an implanted neuronal cell interfaced with an electronic device; an external control module would measure and convert the impulse received by the electronic device from the brain; the external control module would then transmit a signal to a second electronic device interfaced with a prosthesis or robot which undertakes the activity that is imagined or intended. Known methods for measuring brain electrical impulses are described, for example, in U.S. Pat. No. 4,862,359. Methods of controlling robotics or prostheses are disclosed in U.S. Pat. No. 6,171,239 and Amirikian, et al., 1999, Can. J. Exp. Psych. 53:21-34).

Furthermore, the device of the present invention would permit a signal to be sent to the brain from the electronic device. For example, a phototransistor microprocessor array may serve as the electronic device attached to the integrated neuronal cells. The distant neuronal cells attached to an implantable membrane are then transplanted into the lateral geniculate nucleus (LGN) region of the thalamus, which functions as a junction box for visual signals. Elongation of the neuronal cells allows the phototransistor microprocessor array to be exteriorized to receive light impulses outside the cranium. These impulses are then sent deep into the brain by the distant neurons. Behavioral tests and electrophysiologic analysis are performed to evaluate the function of the implant.

Figure 6A:
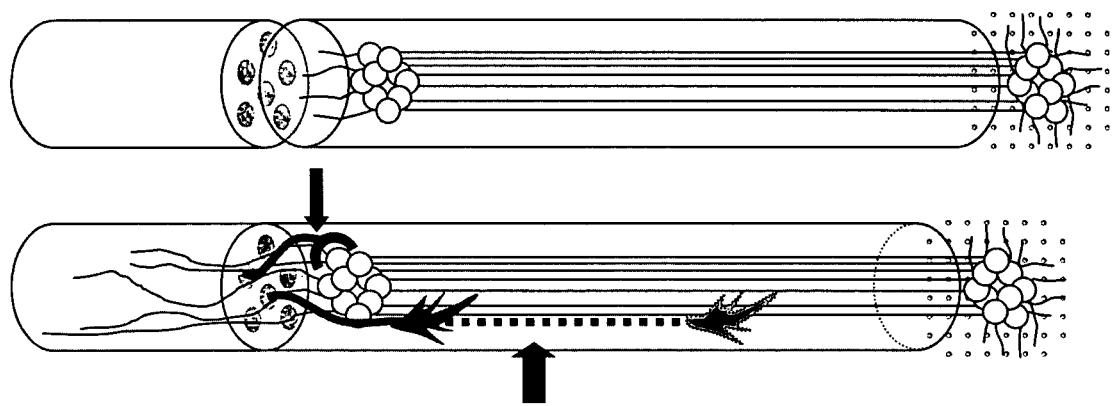
FIGS. 6A and 6B, is a series of schematics of a device and a nerve construct of the invention in a therapeutic application.

In an embodiment, the device is used to neurally control the function of a prosthesis. In this embodiment, the second population of neuronal cells contained on the membrane of the device of the invention is implanted to directly contact a nerve in the peripheral nervous system of a subject, and these neuronal cells are permitted to synaptically integrate with the peripheral nerve (FIG. 6A). The electronic device is interfaced with a prosthetic device. The integrated, transplanted neurons transmit an electrical signal from the central nervous system via the peripheral nerve to the electronic device, which in turn, transmits it to the prosthetic device. The subject with the implanted device of the invention undergoes operant conditioning, using methods known in the art, to assimilate the new axon distribution and control the function the prosthetic device. Willful stimulation of motor fibers are recorded by the electronic device, which in turn drives the prosthesis.

It will be understood that the invention as disclosed herein is operable in many various embodiments, both those disclosed herein and those not explicitly set forth. The skilled artisan, when armed with the present disclosure, will understand the manifold embodiments included within the scope and spirit of the invention, and that such embodiments are equally part of the invention disclosed herein.

In one aspect, the communication is bi-directional, that is, sensor transducers on the prosthesis provide direct stimulation to the electronic device, which in turn, permits excitation of sensory fibers for afferent signaling back to the brain. The type and location of the sensor transducers can be mapped according to the sensory response "felt" by the patient upon stimulation of each electrode in the electronic device. By way of a non-limiting example, stimulation of a specific, individual electrode on the electronic device elicits a sensation of pressure by the patient in a specific region of a phantom finger. A corresponding pressure sensor transducer is therefore positioned in the same region of the finger of the prosthetic limb and is connected directly to that particular electrode on the electronic device. This procedure can be repeated with each electrode of the electronic device to ascertain what type of sensor transducer to use and where to place it on the prosthesis. A result, among others, is that the patient may be able to "feel" where in space the prosthesis is (proprioception), "feel" heat and cold, and "feel" proper strength to grasp an item in order not crush or drop it. This bi-directional communication is unprecedented in current prostheses.

This embodiment takes advantage of the remarkable capacity of the peripheral nervous system to remap afferent and efferent signaling. It also avoids the dangers and risks associated with transplantation of micro-electrodes into delicate nervous tissue. Furthermore, it avoids the non-permissive neuronal growth environment of the central nervous system. Furthermore, tapping into the peripheral nervous system does not require neural decoding; there is little need to computationally interpret complex neural processing from a small region of the brain or spinal cord. The function of any prosthesis may be controlled using the device of the invention. The prosthesis may be transtibial, transfemoral, transradial or transhumeral, among others.

Figure 6B:
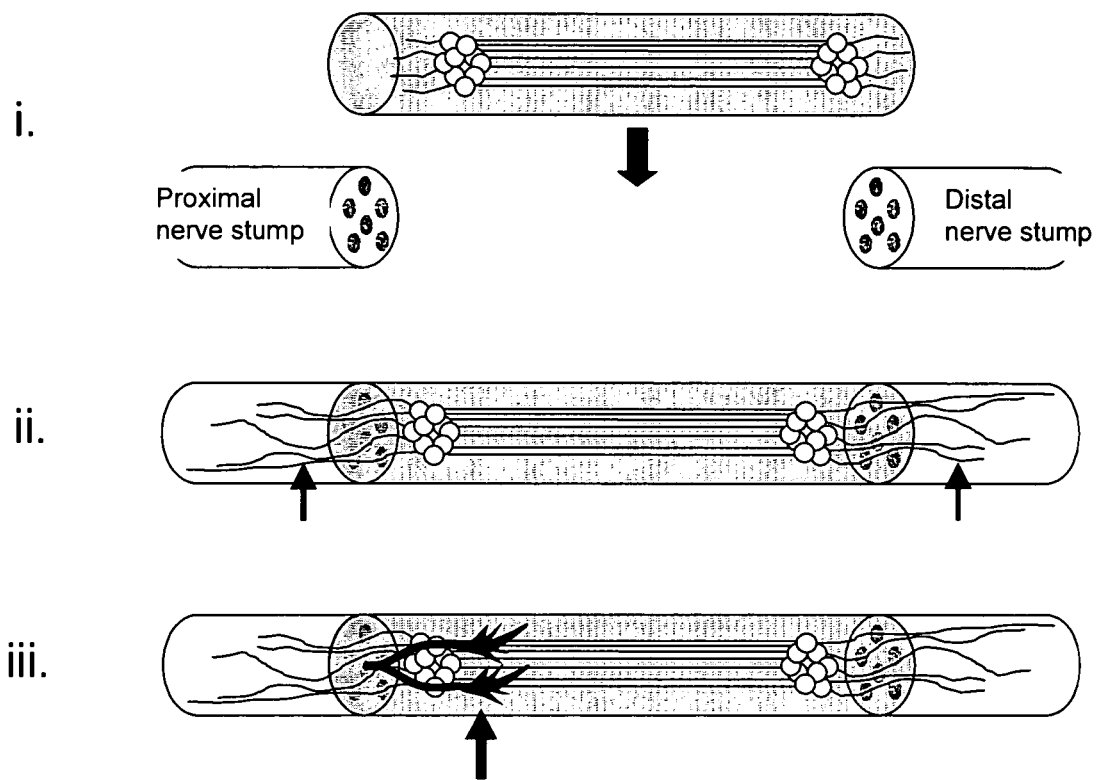

In a therapeutic method using the composition of the invention, a therapeutically effective amount of a nerve construct comprising mechanically elongated neurons and a biocompatible matrix is administered to a subject having a nerve lesion. The composition is administered to a subject by, for instance, transplanting the nerve construct composition into the site of the nerve lesion. See FIG. 6B. Methods for transplantation of the composition of the invention are well known to those of skill in the art of cell transplantation. See, for instance, U.S. Pat. No. 6,365,153, incorporated by reference herein in its entirety. In one embodiment, transplantation of a nerve construct composition involves removing damaged tissue at the site of the nerve lesion and placing the nerve construct composition at the site. In another embodiment, the axons of the nerve construct composition are approximately the same length as the nerve lesion. In another embodiment, the nerve construct placed at the site of a nerve lesion comprises a bioresorbable sheath that is sutured to tissue surrounding the nerve lesion in order to secure the position of the nerve construct. In the therapeutic method, the nerve construct may comprise mechanically elongated neuronal cells from the intended recipient (autologous transplantation), from a genetically identical donor (syngeneic transplantation) or from a non-genetically identical donor (allogeneic transplantation).

The therapeutic methods of the invention may be used with any subject having or suspected of having a nerve lesion. Preferably, the subject is a mammal. In one embodiment, the subject is a veterinary animal, such as, but not limited to, non-human primates, horses, cattle, sheep, dogs, cats, pigs, and goats. In another embodiment, the subject is a human.

As one of skill in the art can appreciate, the composition of the invention, when used in a method to treat a nerve lesion, may reduce the need for extensive axonal regeneration in vivo by providing mechanically elongated living neurons. This is particularly advantageous in regions non-permissive for axonal regeneration, in particular, the CNS. Furthermore, by providing elongated neurons that substantially bridge a nerve lesion, the time to recover from a nerve injury may be significantly reduced. Without wishing to be bound by theory, it is believed that the nerve construct composition of the invention may enable several responses in vivo. First, the mechanically elongated axons in the composition transplanted into a nerve lesion may integrate into the spinal core or peripheral injury site and restore the conduction of nerve signals over the lesion. Second, the elongated neurons may enhance regeneration of endogenous axons by expression of, for instance, novel neurotrophic factors. Third, the elongated neurons may support axon-guided axon growth of endogenous neurons.

The nerve construct of the invention may also be useful in a method of identifying a compound that increases the rate or extent of chemical contact or the extent of physical contact between the mechanically elongated neurons and the endogenous neurons at a nerve lesion. The skilled artisan is familiar with the design of experiments to identify compounds having the desired effect. In brief, the nerve construct is transplanted into a nerve lesion in a model organism and exposed to a test compound. The rate and/or extent of chemical and/or physical contact is assessed by any of the methods well known to the skilled artisan and compared to an otherwise-identical, transplanted construct in the absence of the test compound. A compound that increases the rate and/or extent of contact may be useful as a drug to aid the recovery from a nerve lesion, for instance, when a nerve construct composition of the invention is administered to a subject having a nerve lesion.

EXPERIMENTAL EXAMPLES

The invention is now described with reference to the following Examples. These Examples are provided for the purpose of illustration only, and the invention should in now way be construed as being limited to these Examples, but rather, should be construed to encompass any and all variations, which become evident as a result of the teaching provided here.

Example 1

Embryonic Dorsal Root Ganglion Cell Isolation

Dorsal root ganglia (DRG) were isolated from E15 (E0 is the day after mating) rat embryos. Dissected ganglia were held in Lebovitz L-15 medium during the isolation. Dissociated cultures were treated with 0.25% trypsin (Sigma-Aldrich, St. Louis, Mo.) in a cell dissociation buffer (INVITROGEN™, Carlsbad, Calif.) and incubated at 37° C. for 45 minutes. Trypsin activity was stopped with the addition of L-15 medium+20% fetal bovine serum (FBS; Hyclone, Logan, Utah) and cells were centrifuged at 1000 rpm for five minutes. After discarding the supernatant, the cell pellet was resuspended in 2 mL of complete medium consisting of Neural Basal Medium (INVITROGEN™) supplemented with B27 (INVITROGEN™), 1% FBS (Hyclone), 1 mM L-Glutamine (INVITROGEN™), and 2.5 g/L glucose. The DRGs were then triturated ten times with a fire-polished pipette. Cells were counted and plated on a collagen- or laminin-coated surface at a density of $1-2\times10^6$ cells per mL.

Whole DRGs were plated immediately following isolation in complete media. Plating of whole DRGs allows for very high plating densities and leads to much larger axon fascicles during mechanical elongation. The whole DRGs may be "softened" by a one minute trypsin treatment followed by trypsin inactivation with L-15+20% FBS. Pelleted ganglia are resuspended in complete media gently using a Pasteur pipette and immediately plated.

Example 2

Adult Dorsal Root Ganglion Cell Isolation

The adult DRGs were dissected from adult Sprague-Dawley rats of at least eight weeks of age (Scott, 1977, J. Neurobiol. 8(5):417-27). Briefly, the spinal column was removed from the brain-cervical junction to below L1. Attached tissue and the spinous processes were removed using a pair of roungers. The column was cut with a pair of tough iris scissors starting at the cervical end, cutting through the dorsal roof bone (staying centered as not to damage the ganglia). The column was then separated lengthwise in half by carefully cutting through the cord and ventral side of the column. The spinal cord and menengies along the inner spinal column were removed using fine forceps and the DRGS were pulled from the foramen. Using small spring scissors, the nerves on both sides of the DRG were cut. Two incisions were made on each side of ganglia and placed into bovine serum albumin (BSA) coated tubes containing L-15 medium during the isolation.

Adult DRGs are myelinated and must be dissociated to separate the neurons from the surrounding tissues and supporting cells. Dissected DRGs were treated in 0.25% collagenase-P (Boehringer Mannheim, Germany) in Neural Basal medium for 1.5 hours. All the DRGs and tissues were pelleted and resuspended in 0.25% trypsin in cell dissociation buffer for an additional 1.5 hours. Trypsin activity was stopped with 20% FBS in Neural Basal medium and the cells were centrifuged. The pellet was resuspended in complete medium and mechanically separated using a fire-polished Pasteur pipette until the DRGs were completely dissociated.

An almost pure suspension of DRGs was obtained by passing the dissociated product through a BSA gradient. A two-layer BSA gradient (5% and 10%) was prepared by adding 5 mL of a 5% BSA solution in a 15 mL centrifuge tube. Using a Pasteur pipette, the second layer was added below the 5% BSA by slowly pipetting the 10% BSA solution with the Pasteur pipette tip at the bottom of the tube. The 5% BSA floats on top the 10% BSA. The dissociated DRG suspension was carefully placed on top of each gradient by adding it drop by drop along the side of the tube. The gradient tubes were centrifuged at 100×g for seven minutes. Most of the DRG cells and non-neuronal cells pelleted while the myelin and Schwann cells were found in the upper fractions of the gradient. Pellets were resuspended in 5 mL of complete media, and carefully placed on a second BSA gradient prepared as described. The gradients were centrifuged at approximately 90×g for no more than five minutes. This centrifugation step removed most of the smaller non-neuronal cells from the larger DRG cells. The pellets were resuspended in complete medium, counted and plated.

Example 3

Axon Elongation Device

Dorsal root ganglion cell axons were grown by tension induced elongation (Smith, et al., 2001, Tissue Eng. 7:131-138). The device consistently separates two adjoining substrates on which neural cells are cultured. The adjoining substrates were placed such that axons growing in culture could grow across the interface between the two substrates easily. The bottom substrate, an electronic device, was placed in the bottom of the elongation device on which a stationary population of neurons was cultured. An overlapping ACLAR® substrate (Honeywell International Inc., Morristown, N.J.), i.e., the towing substrate, was placed on top of the electronic device substrate and served as the moving population of cells. Once the neurons and their axons matured and synapsed across the bottom and towing substrate interface, the two substrates were separated using a micro-stepper motor system (Smith, et al., 2001, Tissue Eng. 7:131-138; U.S. Pat. No. 6,264,944). The result was two populations of cell bodies connected together via elongated fascicular axon tracts.

Example 4

Elongation Device Preparation, Plating, and Maintenance

Cell culture plates, the ACLAR® surface, and the electronic device were coated with collagen prior to DRG plating. After ACLAR® was cut into desired sizes, it was washed with laboratory soap and rinsed well. ACLAR® was then treated in 1 M NaOH for 24-48 hours, rinsed well in sterile water, then bathed in 100% ethanol for 10 minutes. The ACLAR® was then allowed to dry on a sterile rack in a cell culture hood. The ACLAR® substrate was attached to the elongation device framework using medical grade RTV silicone (NuSil, Carpinteria, Calif.). During curing, RTV silicone releases acetic acid, which can be lethal to cells, therefore the silicone was allowed a minimum of three days to completely cure prior to plating cells. Twenty-four hours after assembly, the ACLAR® surface was treated with 10 µg/mL poly-L-lysine (PLL) for 4 hours. The PLL solution was removed and the ACLAR® was allowed to dry for one hour and the surface was subsequently rinsed three times with sterile water. After the silicone has completely cured, the ACLAR® surface was coated with type 1 rat-tail collagen (Becton Dickinson, Franklin Lakes, N.J.). Collagen was spread over the surface (10-20 µl per cm$^2$) and polymerized by exposure to ammonia vapors for two minutes. The collagen was then allowed to dry completely in a cell culture hood before plating cells. The electronic device was sterilized and coated with collagen in a similar manner.

The hydrophobic collagen surface provides that cells can be plated in any desired arrangement by applying the cell suspension in a puddle and allowing the cells to attach for about 2-4 hours before the chamber is flooded with media.

Embryonic, dissociated cells cultures were plated at a density of 1-2×10⁶ cell per ml of which 500 μl was plated along the adjoining substrate interface of the elongation device. Whole embryonic DRGs were plated from 6-8 pups in 500 μl of complete medium along the substrate interface of the elongation device. Dissociated DRG cells from one adult rat were resuspended in 1 ml of complete medium of which 500 μl was plated on each of two elongation devices.

After cell attachment, the elongation device chamber was flooded with complete medium with mitotic inhibitors, 10 μM FdU and 10 μM Uridine. The media was changed every two to three days and the mitotic inhibitors applied once a week. On day five, the elongation device was turned on and left undisturbed without changing the medium. For long-term experiments, the media was changed once a week.

Example 5

Axon Elongation Scheme

Five days after plating, the DRG cells were elongated. Elongation was controlled by displacement of the towing membrane. Since stretch-induced growth was initially strain limited, elongation began at a slow rate and was increased to the desired growth rate. Stretch rate was programmed into the motion control device by choosing a displacement, and a resting time in a step-wise fashion. For example, 1 mm/day was programmed as 1 μm displacements every 86.4 seconds.

Elongation started at 1 mm/day (1 μm every 86.4 seconds) for the first 24 hours. The elongation rate was then increased by 1 mm/day every 6 to 12 hours until the maximum elongation rate was achieved. In the case of a maximal rate of 8 mm/day, the ramping was slower and at 12 to 24 hour intervals to allow the axons to increase in length.

Example 6

Tissue Fixation, Immunocytochemisty and Electron Microscopy

For immunocytochemistry, the elongated tissue was fixed with 4% paraformaldehyde for 60 minutes. Following three rinses in phosphate-buffered saline (PBS), elongated axons were blocked with 4% Normal Goat Serum (NGS) in PBS at room temperature for 60 minutes. The primary and secondary antibodies were applied in 4% NGS, 0.1% Triton X in PBS for 60 minutes each. Primary antibodies targeted to the 200 kDa neurofilament fragment were NF200, diluted 1:400 (Sigma-Aldrich, St. Louis, Mo.), and SMI-32, diluted 1:400 (Sternberger Monoclonals, Lutherville, Md.). Antibodies to β-tubulin were SMI-61 & 62, diluted 1:400 (Sternberger Monoclonals, Lutherville, Md.) and the antibody to tau, diluted 1:400 (Dako, Denmark). Fluorescent secondary antibodies were used according to manufacturer's instructions (Molecular Probes, Eugene, Oreg.).

Immunocytochemistry of the elongated fascicular axon tracts revealed a normal cytoskeleton containing phosphorylated neurofilament, tau and β-tubulin protein expression. The results indicated that the heavy neurofilament (NF—H, 200 kDa) was present throughout the entire elongated axon length. All axons studied showed the same result over several studies and at each rate and length. Antibodies to the phosphorylated NF—H (SMI-32) and a non-specific NF-200 antibody had significant reactivity in all elongated axons. β-tubulin was also identified using the SMI-61 and SMI-62 antibodies for unassembled and assembled β-tubulin, respectively. Moreover, tau protein expression, which is reportedly the slowest of the transported cytoskeletal proteins, was found in significant amounts throughout each and every elongated axon. Similar results were found for adult DRG elongated axons.

For transmission electron microscopy, elongated axons were fixed in 4% paraformaldehyde, 2% glutaraldehyde, in 0.1 M sodium cacodylate buffer, overnight at 4° C. To prevent any damage to the axons during their removal from the elongation device, the tissue was supported in 2% agar. Melted agar was allowed to cool to approximately 45° C. then gently pipetted over the tissue. The agar was allowed to cool and harden at 2° C. With a #11 scalpel, the substrates were carefully cut loose and the tissue removed. The tissue was then washed in the same buffer and post-fixed in 1% osmium tetroxide for 1 hour at 4° C. After another buffer wash, the sample was dehydrated in a graded ethanol series before infiltration and embedding in epoxy resin (EMbed-812; Electron Microscopy Sciences, Fort Washington, Pa.). Thin sections were cut at 800 Å and placed on formvar-coated grids. After staining with uranyl acetate and lead citrate, sections were examined with a JEOL 100CX transmission electron microscope.

For scanning electron microscopy, elongated axons were fixed in 4% paraformaldehyde, 2% glutaraldehyde, in 0.1 M sodium cacodylate buffer, overnight at 4° C. The sample was rinsed and post-fixed in 1% osmium tetroxide for 30 minutes. After another buffer wash, the sample was dehydrated in a graded ethanol series followed by a drying step of two applications of hexamethyldisilazane (HMDS; Electron Microscopy Sciences, Fort Washington, Pa.) of ten minutes each.

Transmission electron micrographs were prepared for the cross-sections of both stretch-induced elongation and growth cone induced growth of DRG axons. Microtubules were counted and cross-sectional areas were measured. The results showed that stretch-induced axon elongation leads to a hypertrophy of axonal caliber. On average, the axon cross-sectional area increased by 30% and the median cross sectional area increased by almost 50%.

Observations from Examples 1-6

Figure 2A:
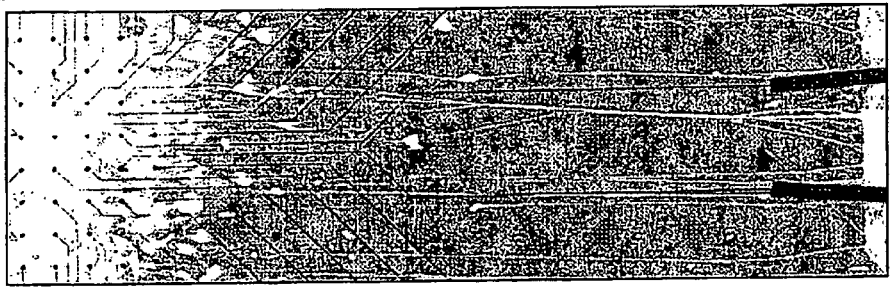
FIGS. 2A and 2B, show integrated elongated neurons attached to a multi-electrode array.
Figure 2B:
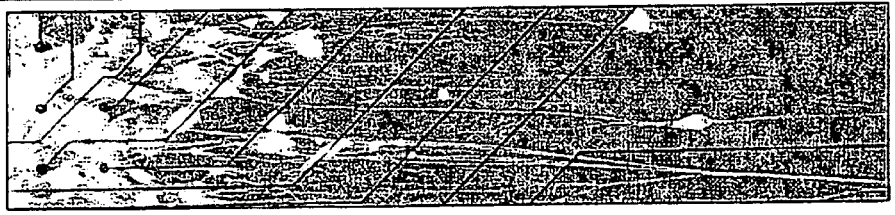

Using the method of the invention, rat dorsal root ganglion were attached to a membrane and a multi-electrode array electronic device (FIGS. 2A and 2B). It was found that dorsal root ganglion cells could be elongated to lengths of over three to five centimeters at an average rate of six millimeters per day. The maximal rate obtained was eight mm/day sustained for 24 hours with no evidence of axonal breakage or damage. Modified elongation devices may be engineered to produce neuronal cells elongated to lengths of 15 cm or greater.

Short axon segments were found to be very sensitive to the rate of stretch-growth. If axons were allowed to grow at a slow to moderate rate for several days, the axons could be ramped to higher stretch rates without axonal damage. Axons that were grown for one day at a rate of 1 mm/day and then ramped to 6 mm/day showed a significant amount of axonal breakage after 2 days. However, if the axons were allowed to elongate for a period of 3 days at 1 mm/day and then ramped to 6 mm/day, there was no evidence of axonal breakage.

As demonstrated herein, adult and embryonic DRG cells were elongated. Adult DRG cells took longer to initiate regenerative growth in culture following dissection and dissociation. Approximately one additional week in culture, compared to embryonic cells, was required for adult DRGs to grow sufficient axons across the elongation interface. Adult DRG cells also were constrained to a slower rate of elongation; a maximum of 1 mm/day for 7 days was attainable.

Example 7

Extreme Stretch Growth of Integrated Axons

The materials and methods used in this example are now described.

Cell Culture: Dorsal root ganglion (DRG) explants from 8-10 E15 rat embryos (Charles River, Wilmington, Mass.) were isolated as described by (Kleitman et al., 1998, "Tissue Culture Methods for the Study of Myelination" In: Culturing Nerve Cells, 2nd Edition (Banker G, Goslin K, eds), MIT Press, Cambridge, Mass.). Isolated explants were then plated, approximately one half of explants on each of the two adjacent membranes of the elongation device. Cultures were maintained in complete medium consisting of Neural Basal Medium (INVITROGEN™) supplemented with B27 (INVITROGEN™), 1% FBS (Hyclone, Logan, Utah), 0.4 mM L-Glutamine (INVITROGEN™), 2.5 gm/l glucose, and 10 ng/ml 2.5S nerve growth factor (Becton Dickinson, Bedford, Mass.). All cells were allowed to attach for 4 hours before the elongation device chamber was filled with complete medium containing the mitotic inhibitors (mitotitic inhibitor 1 (MI#1): 5 μM cytosine β-D-arabinofuranoside (AraC, Sigma, St. Louis, Mo.), 20 μM 5-fluoro-2'-deoxyuridine (5FdU, Sigma) and 20 μM uridine (Sigma)). After 2 days, the medium was exchanged with complete medium plus the mitotic inhibitors (MI#2: 20 μM 5FdU and 20 μM uridine) for 3 days. Thereafter the media was changed every two to three days and MI#2 was reapplied once a week.

At all times the principles enumerated in the "Guide for the Care and Use of Laboratory Animals" prepared by the Committee on Care and Use of Laboratory Animals of the Institute of Laboratory Service, National Research Council were strictly adhered to. The University of Pennsylvania Institutional Animal Care and Use Committee have approved the protocols.

Figure 3:
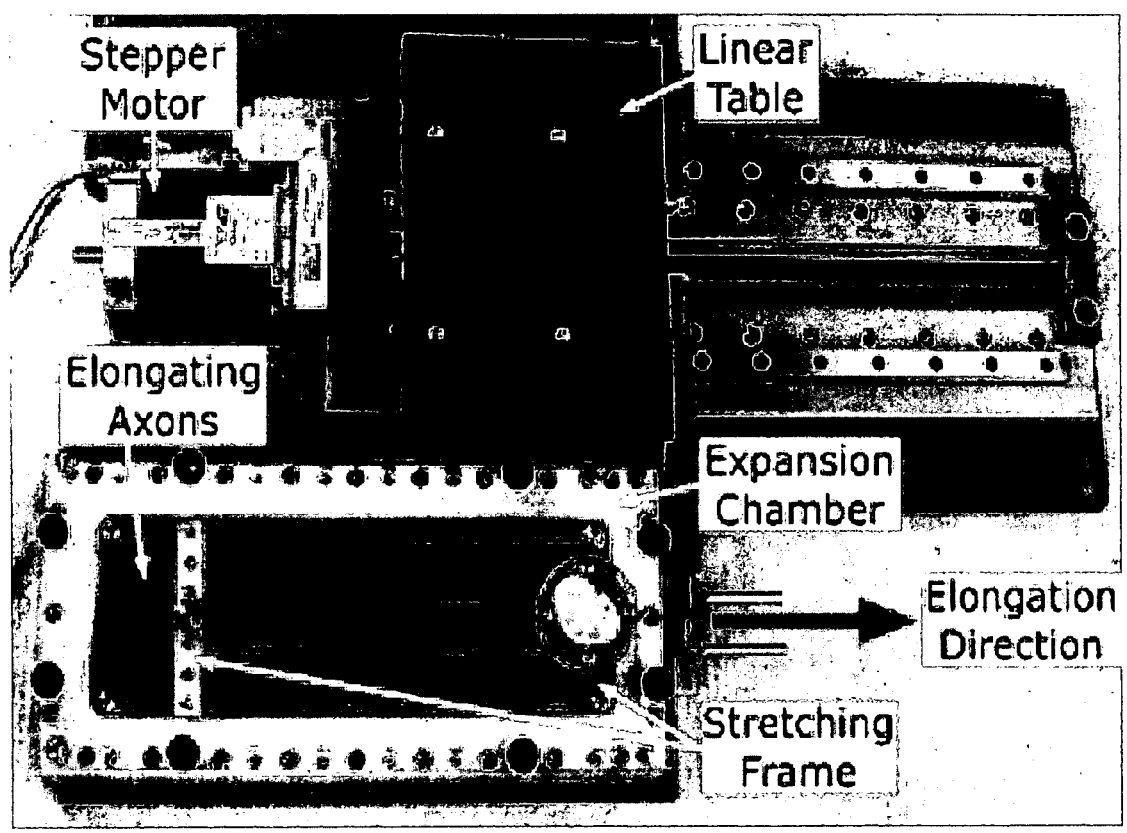
FIG. 3 is an image of an axon elongation device. The system comprises a custom-designed axon expansion chamber, linear motion table, microstepper motor and controller. The expansion chamber is a sealed enclosure with a removable axon-stretching frame and gas exchange port. The entire system fits within a typical $CO_2$ incubator.
Figure 4:
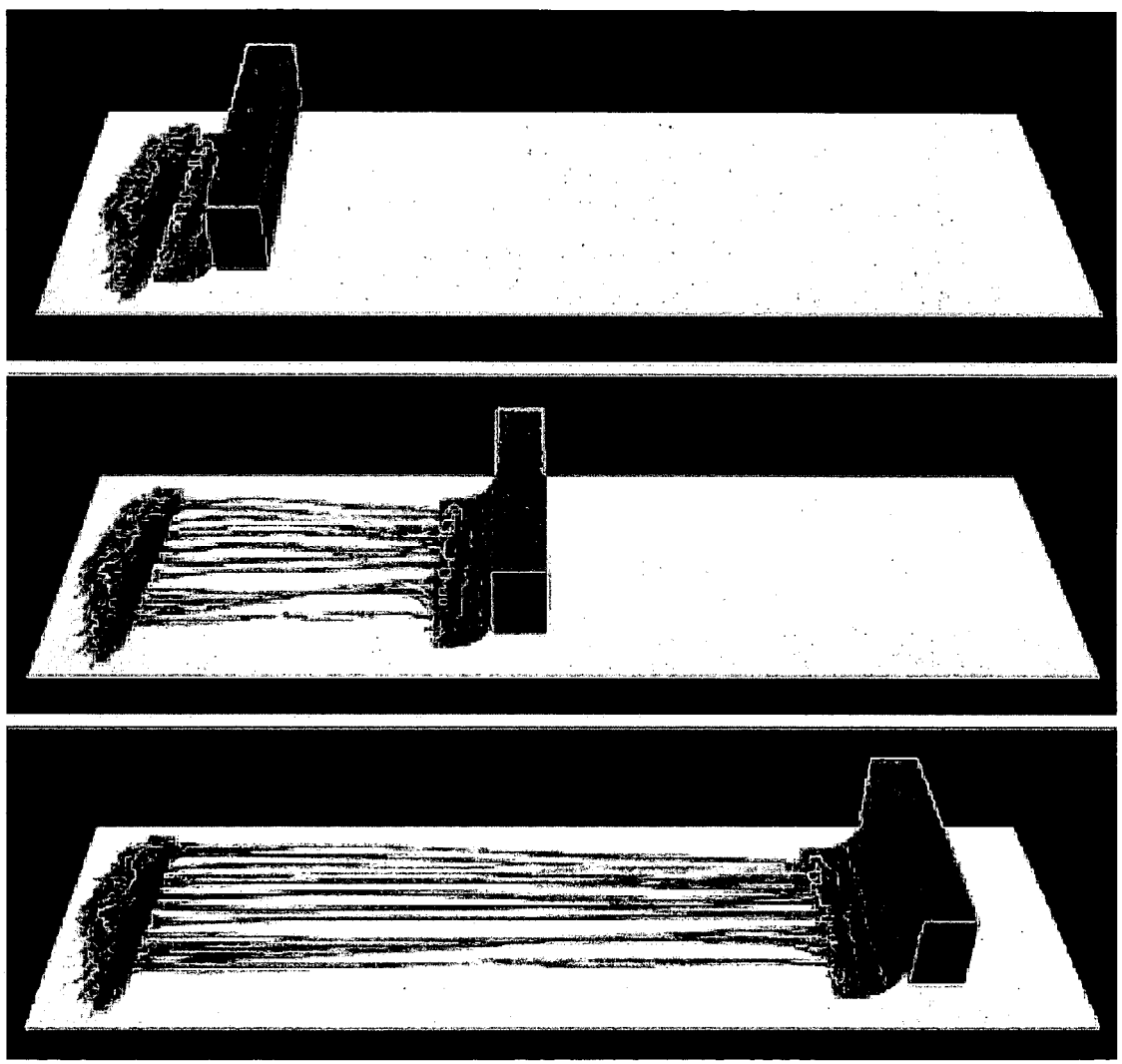
FIG. 4 is a series of schematic images illustrating extreme axon stretch-growth. The rectangular element is the towing bar attached to the top membrane (towing substrate). The bottom membrane is underneath the neurons on the left and the entirety of the elongating axons. The top panel image depicts dorsal root ganglion plated on two adjacent membranes and allowed to grow for 5 days across the interface to form interconnected neuron populations. The middle and bottom panels illustrate the stretched axons of the dorsal root ganglion after gradual separation of the two interconnected neuron populations. The bottom panel depicts stretch axons after a longer period of stretch conditions compared to the middle panel. The towing substrate is moved by a computerized step motor system.

Elongation Device:

The axon stretch-growth system is composed of a custom-designed axon expansion chamber, linear motion table, and controller (see FIG. 3). The expansion chamber is a sealed enclosure with gas exchange port that fits within a typical $CO_2$ incubator. It contains a removable axon stretching frame that arranges two adjoining membranes in an overlapping fashion on which neurons can be cultured. The bottom membrane (198 μm thick), made of optically transparent ACLAR® 33C film (Structure Probe, West Chester, Pa.), covers the entire bottom of the elongation device on which the stationary population of neurons is cultured. An overlapping movable ACLAR® membrane (approximately 10 μm thick) is placed on top of the bottom membrane and serves as the moving population of cells. Axons developing in culture can easily grow across the interface between the overlapping membranes interconnecting the neurons on both sides (see FIG. 4). Axons bridging the two membranes were stretched by displacing the top membrane across the lower stationary membrane using a microstepper motor system (Servo Systems, Montville, N.J.). Prior to assembly, ACLAR® was washed, treated in 1 M NaOH for 24 hours, and then sterilized in 100% ethanol for 10 minutes. ACLAR® membranes were attached using medical grade RTV silicone (NuSil, Carpenteria, Calif.) and then treated with 10 μg/ml poly-L-lysine (PLL). Type 1 rat-tail collagen (Becton Dickinson, Franklin Lakes, N.J.) as supplied was spread over the surface (10-20 μl per $cm^2$) and polymerized by exposure to ammonia vapors for 2 minutes and then allowed to dry completely before plating cells. The hydrophobic collagen surface allows for cells to be plated within any desired arrangement by applying the cell suspension in a defined puddle. DRG explants were plated and maintained as described above.

Axon Stretch Growth:

In order to stretch isolated axons, rat primary DRG neurons were plated on two adjacent membranes within an elongation chamber. Routinely, DRG neurons were given five days after plating for axons to extend between the two membranes by growth cone-mediated elongation. This growth formed a bridge of axons approximately 100 μm long, integrating the neuron populations on each membrane. Bridging axons were stretched by slowly separating the two membranes via a microstepper motor (see FIG. 4). The stretch rate was programmed into the motion control system by implementing a displacement step and a resting time in a stepwise fashion. Here, the net rate of axon elongation is expressed in units of millimeters per day. For example, the initial stretch rate of 1 mm/day was the net result of 2 μm displacements every 172 seconds. Subsequent increases in the net stretch rate were applied by increasing the size of the displacement step or reducing the resting time.

To determine the optimal stretch-growth parameters during the initial 24 hours of elongation, the displacement steps and resting times were varied in a stepwise fashion. In each experiment, cultures were examined after 24 hours of elongation for evidence of axon rupture. Based on initial studies, the experimental matrix maintained a net rate of elongation of 1 mm/day over the first day and began with displacement steps of 3.5 μm every 300 seconds. At these parameters, stretch growth occurred, but with some evidence of axon disconnection. In each subsequent experiment, the displacement step was reduced in 0.5 μm increments (resting time was adjusted to maintain a net elongation rate of 1 mm/day) until there was no further evidence of axon disconnection. The maximum net rate of elongation was then investigated to determine whether the initiation of stretch-growth could exceed 1 mm/day. The displacement step was reduced to the minimum resolution of the elongation system (0.5 μm per step). The net elongation rate was gradually increased above 1 mm/day by reducing the resting time until axon disconnection was observed.

After the initial 24 hours of growth, the net rate of axon elongation was increased by 1 mm/day every 48 hours until the desired plateau growth rate was reached. The cultures were examined each day, and maximal rate increases were determined according to whether the axon tracts disconnected or continued elongating. When a paradigm was successful, the stretch rate was increased more frequently (every 24, 12, 6 hours, and so on) until axon rupture was observed. If visual damage to the axons was noted, the rate increase strategy was reformulated over a longer time period. The desired rate of stretch growth was considered successful if axons could sustain that rate for a minimum of 24 hours without evidence of axon disconnection. Furthermore, experiments were performed to determine if rate accelerations larger than 1 mm/day could be tolerated. Rate increases up to 4 mm/day were limited to 1 mm/day, but subsequently the rate could be escalated by steps of 2 to 4 mm/day.

Specimen Preparation and Analysis:

For transmission electron microscopy (TEM), elongated axons were fixed in 4% paraformaldehyde and 2% glutaraldehyde in 0.1 M sodium cacodylate buffer overnight at 4° C. To prevent damage to axons during their removal, the tissue was supported within 2% agar and then cut loose from the elongation device using a scalpel. The tissue was post-fixed in 1% osmium tetroxide for 1 hour at 4° C., dehydrated in a graded ethanol series before infiltration and embedding in epoxy resin (EMbed-812, Electron Microscopy Sciences, Fort Washington, Pa.). After staining with uranyl acetate and lead citrate, sections were examined with a JEOL 100CX transmission electron microscope.

For scanning electron microscopy (SEM), elongated axons were fixed in 4% paraformaldehyde and 2% glutaraldehyde in 0.1 M sodium cacodylate buffer overnight at 4° C., post-fixed in 1% osmium tetroxide for 30 minutes and dehydrated in a graded ethanol series followed by a drying step of two, ten-minute applications of hexamethyldisilazane (Electron Microscopy Sciences). For image analysis, cross sectional areas were measured for each axon using Scion Image (Scion Corporation, Frederick, Md.).

The results of the experiments presented in example 7 are now described.

Figure 7:
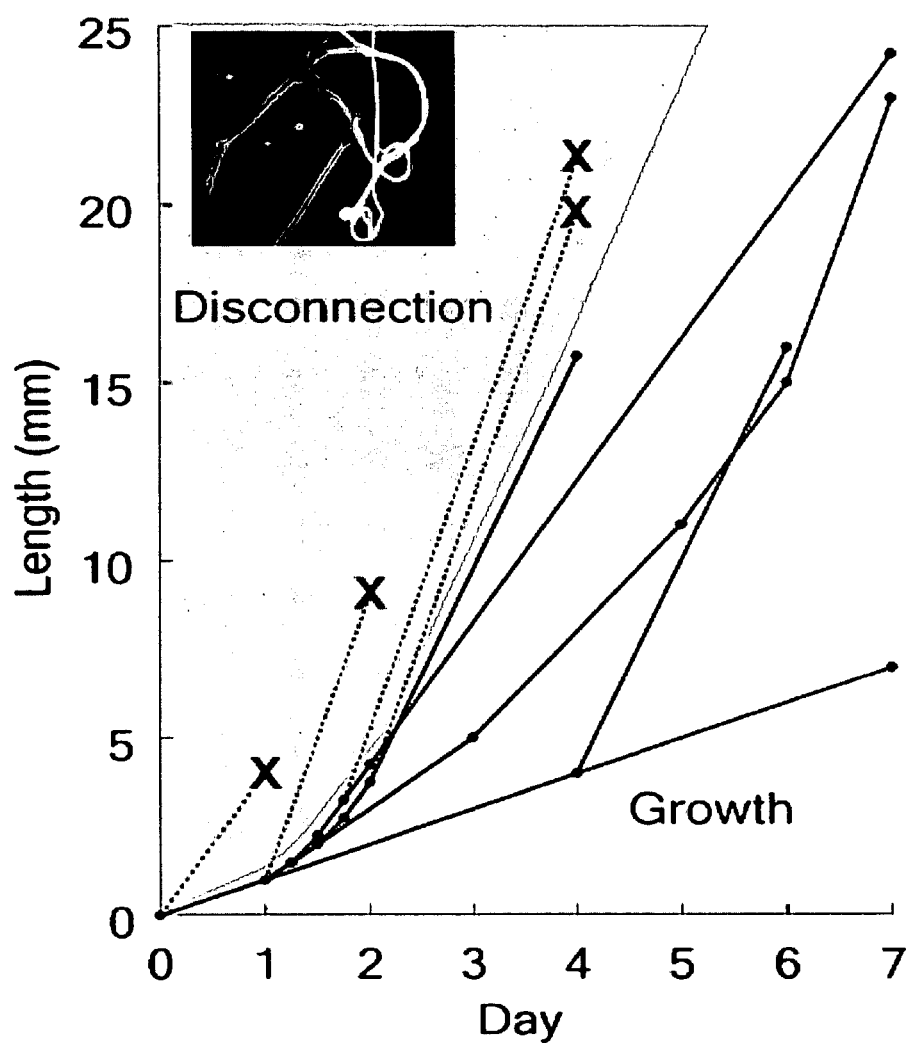
FIG. 7 is a graphic representation of stretching conditions that define the boundaries of axon growth or disconnection. Each line represents individual paradigms of accelerating displacement (elongation) of integrated axon tracts in culture. X's in shaded area denote disconnection of axon tracts during stretching. Lines without X's represent successful growth of axon tracts in response to escalating stretch rates up to 8 mm per day. Inset figure shows a disconnected axon labeled with an antibody against phosphorylated neurofilament protein.

It was discovered that axon tracts can undergo extreme stretch-growth under conditions of rapid as well as long-term mechanical elongation. However, there were clear boundaries that lead to either growth or disconnection (FIG. 7). The thresholds of axon stretch-growth were determined by performing over one hundred individual experiments evaluating a range of stretch rates escalated over several days and sustained elongation over a few weeks. Stretch-growth paradigms were considered successful if axons continued to elongate and there was no evidence of disconnection. Optimal conditions were found to be dependent on two parameters: 1) the size and frequency of displacement steps at a fixed stretch rate, and 2) the time period for acclimation to each increase in the net rate of elongation.

Over the first 24 hours of stretch-growth, axon tracts could be expanded without disconnection at a maximum elongation rate of 1 mm/day, representing an approximately 10-fold increase over their original length. However, disconnection was closely associated with the strain applied to axons, and growth could only be achieved through a gradual motion consisting of small and frequent displacement steps. Through a stepwise analysis, the optimal stretch parameters for the net elongation rate of 1 mm/day were found to be 2 µm displacements every 172 seconds. This represents about 2% of applied strain at the start of elongation when axon measured approximately 100 µm. Stretch rates equivalent to 1 mm/day consisting of larger displacement steps and longer resting times lead to rupture of the axon tracts, whereas reducing displacements smaller than 2 µm provided no further benefit. In addition, regardless of the size and frequency of the displacement steps, stretch rates beyond 1 mm/day resulted in disconnection during the first day of elongation.

Following the 24 hour initiation period, axons tolerated progressively greater rates of elongation as long as sufficient acclimation time was allowed between increases in the net rate. Due to the substantial growth in axon length after 24 hours of stretch, applied strain had rapidly decreased from 2% to 0.2%. However, axons would readily disconnect if elongation rates were stepped up too rapidly even though the associated increase in strain was small. It was found that net increases of 1 mm/day required 12 hours or more of acclimation until a rate of 4 mm/day was reached. Thereafter, the stretch rate could be increased by a step of up to 4 mm/day (FIG. 5). This approach resulted in an exceptional growth rate of 8 mm/day, which was sustained for 24 (n=10) to 48 hours (n=2) without evidence of disconnection (FIGS. 5 and 6). This was the highest rate evaluated and there was no evidence that even greater rates could be achieved.

Figure 8:
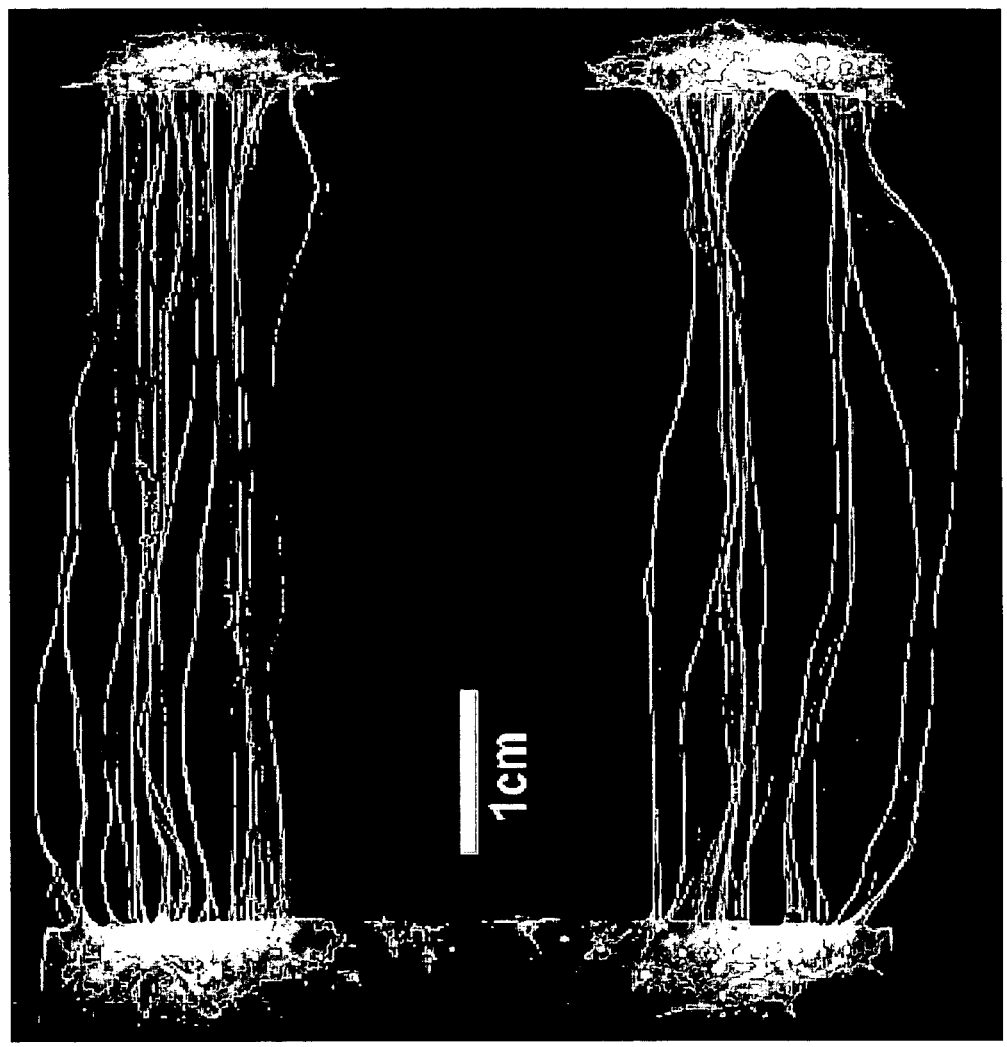
FIG. 8 is an image of axon tracts stretch-grown to 5 cm long. Axon tracts (vertical lines in middle of image) bridge two populations of neurons (at top and bottom of image). Prior to the initiation of stretch-growth, the two populations of neurons were adjacent and the bridging axons were approximately 100 μm long. (Color inverted for clarity.)

It was also observed that stretch-growth of axons could be maintained over several weeks in culture, producing axon tracts of unprecedented lengths. Axons were continuously extended at the rate of 4 mm/day over 14 days, resulting in 5 cm long axon tracts (n=5) (FIG. 8), or over 28 days reaching a length of 10 cm (n=1). In each preparation, the total number of elongating axons was estimated to be $10^5$-$10^6$, with fascicles large enough to be seen easily with the naked eye.

Figures 9A, 9B, 9C, 9D:
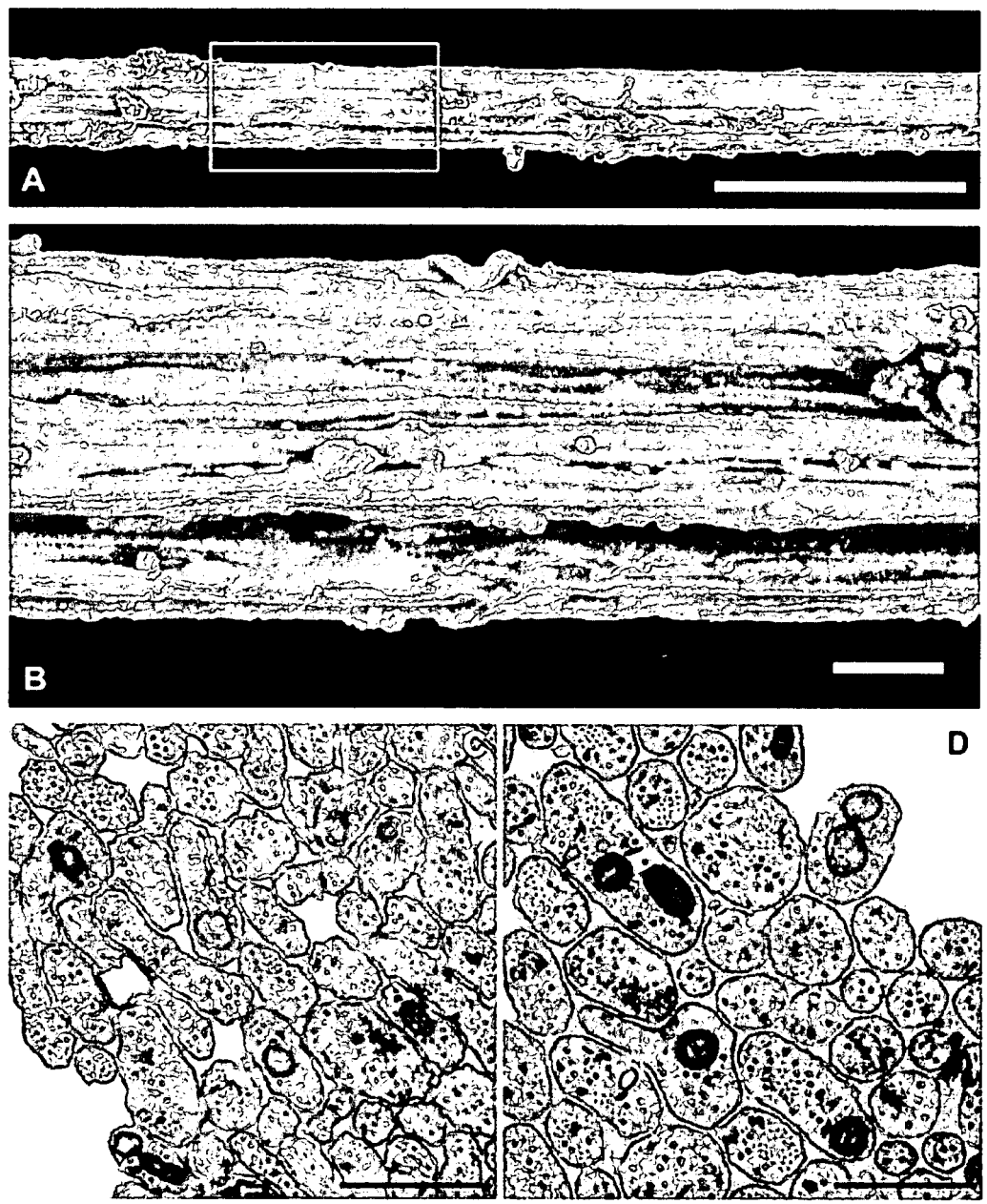
FIGS. 9A-9D, is a series of electron microscopy images.
Figure 10A:
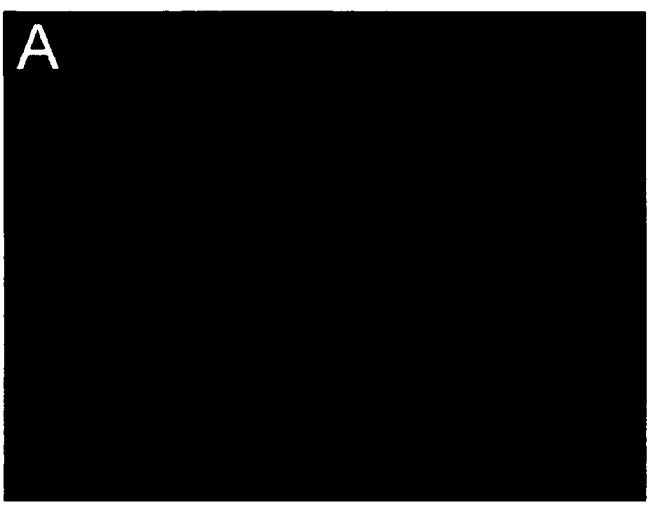
FIGS. 10A-10D, depicts images of fluorescent micrographs of immunostained adult human DRG neurons in culture. Ganglia are shown with elaborate axonal networks. Cultures were maintained for over three months. Human DRG neurons were plated on dishes coated with PLL (Sigma) and were immunostained with antibodies specific for DRG neurons.
Figure 10B:
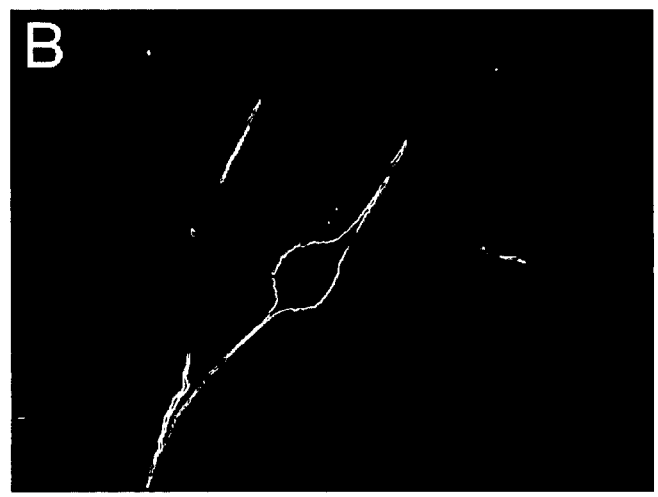
Figure 10C:
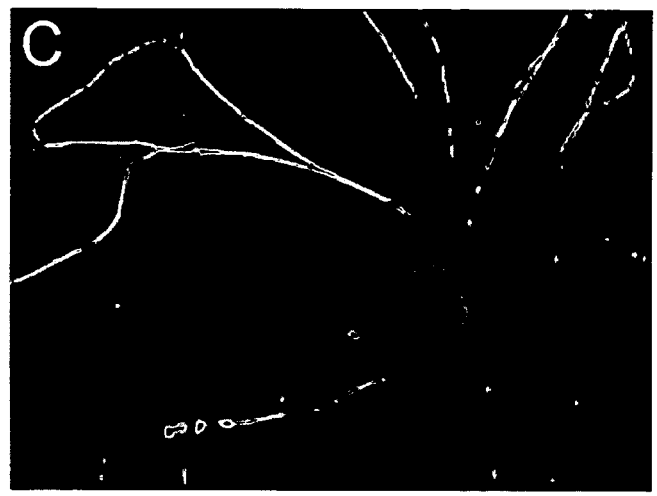
Figure 10D:
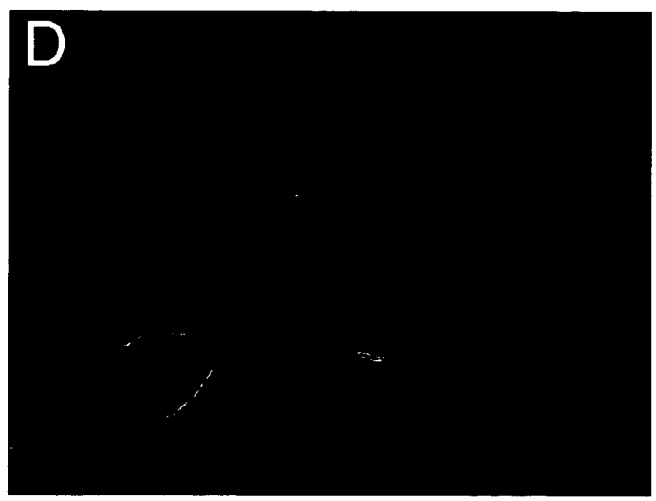

Actual growth of the elongated axon tracts was confirmed by analyzing their structure with electron microcopy. SEM examination of the longitudinal aspect of elongated cultures demonstrated that the axons were highly organized in large tracts arranged in parallel to each other. Initially axons were oriented in a web of small fascicles, which coalesced into larger tracts as they elongated (FIGS. 9A and 9B). Axons appeared uniform along their lengths, and there was no evidence that the axons were thinning out or redistributing axonal constituents due to stretch. To examine the axon ultrastructure, TEM images were acquired from cross sections of axons stretch-grown to 5 cm and "static" non-stretched axons taken near the center of the axon length; the furthest distance from the soma (FIGS. 9C and 9D). Cross-sectional areas of approximately 2000 individual axons were measured from 50 images taken from 4 individual regions. Surprisingly, the average cross sectional area was 35% larger for the elongated axons (0.58 µm$^2$) compared to static axons (0.43 µm$^2$, $p<0.01$). Axonal ultrastructure displayed the typical morphology and density of key structural elements and organelles found in static controls. Microtubule density remained constant at 153/µm$^2$ for static controls and 158 µm$^2$ ($p<0.01$) for stretch-grown axons. In addition, neurofilament organization appeared unchanged, mitochondrial morphology was normal, and there was no change in the number of mitochondria. Furthermore, there was no evidence observed of stretch-growth induced axonal pathology, such as loss or interruption of cytoskeletal structure or the accumulation of proteins due to disruption of axonal transport.

Example 8

Stretch Growth of Human Dorsal Root Ganglia Neurons

The materials and methods used in this example are now described.

Tissue Harvesting:

In this study, two different avenues were used to acquire human DRGs, both fully approved by the Institutional Review Board at the University of Pennsylvania. First, a protocol to grow DRG neurons that are harvested from patients undergoing bilateral C2 ganglionectomy for treatment of occipital neuralgia was developed. Immediately after the DRGs have been removed during the elective surgery, the tissue was placed in cold Hibernate A medium (INVITROGEN™), stored on ice and taken to the laboratory for further processing.

Second, DRGs were acquired from organ donors through the Gift of Life (GOL) program, the Philadelphia region's organ and tissue transplant network. The donors were patients that were less than 60 years old who met brain death criteria and had a negative serology for HIV. In close cooperation with the GOL program, DRG isolation was added to the consent form for all organ donors in the region. After the major organs were harvested by the respective organ transplant surgeons, the Neurosurgery team harvested DRG through the same anterior incision used for organ harvesting. An anterior two-level corpectomy was performed at the mid-thoracic level to expose the spinal cord. The DRG was identified at its entrance to the dorsal-lateral spinal cord and incised with a blade. The average length of time it took for harvesting four DRGs (two at each level) was 20 minutes. Following the harvesting, the entire thoracic incision was closed in anatomical layers. Sterility was maintained throughout the entire procedure. Immediately after the harvest, the DRG tissue was placed in cold Hibernate A solution, stored on ice and taken to the laboratory for processing.

DRG Cell Culture:

Under the microscope, ganglia were cleaned of excess fat, connective tissue, and nerve roots, and then sliced into small pieces. The pieces were mildly digested in an enzyme cocktail of 0.25% Collagenase P (Roche Diagnostics, Basel, Switzerland) and 0.1% Dispase I (Roche Diagnostics) and incubated overnight at 37° C. for 18 hours. Following digestion, the cells were washed free of the enzyme solution with Hank's Balance Salt Solution (HBSS). DRGs were separated from myelin debris and non-neuronal cells using a density gradient of 5% and 10% fetal bovine serum. After purification, cells were plated onto dishes or used for axon stretch-growth experiments.

Cells were maintained in Neurobasal-A media (INVITROGEN™) supplemented with B-27 Supplement (INVITROGEN™), Penicillin/Streptomycin (INVITROGEN™), 0.4 mM L-glutamine (Sigma, St. Louis, Mo.), glucose (Sigma), 10 ng/ml 2.5S nerve growth factor (Becton Dickinson, Bedford, Mass.), and 1% fetal bovine serum (Hyclone, Logan, Utah). Cultures were treated with the mitotic inhibitors (MI#1: 5 µM cytosine β-D-arabinofuranoside, 20 µM 5-fluoro-2'-deoxyuridine and 20 µM uridine (Sigma) on the day of plating. After 2 days, the medium was exchanged with one including the mitotic inhibitors (MI#2: 20 µM 5-fluoro-2'-deoxyuridine (Sigma) and 20 µM uridine (Sigma) for 3 days. Thereafter the media was changed every two to three days and the mitotic inhibitors MI#2 were applied once a week.

Electrophysiology:

The whole cell variant of the patch clamping technique was performed using an Axopatch 1 D patch clamp and DIGIDATA® data acquisition system (Axon Instruments, Union City, Calif.). All experiments were performed at room temperature. External bathing solution was continuously perfused across the tissue and consisted of 115 mM NaCl, 5.6 mM KCl, 2 mM $CaCl_2$, 1 mM $MgCl_2$, 11 mM glucose, 1 mM $NaH_2PO_4$, and 25 mM $NaHCO_3$. While measuring DRG potassium currents, sodium channels were inhibited using 1 mM lidocaine. Internal pipette solution consisted of 5 mM NaCl, 155 mM KCl, 1 mM $MgCl_2$, 3 mM EGTA, 10 mM HEPES, and adjusted to pH 7.3. While measuring DRG sodium currents, potassium currents were eliminated by altering the internal solution to 143 mM CsCl, 1.21 mM $CaCl_2$, 1.21 mM $MgCl_2$, 6.04 mM Na HEPES, 3.96 mM HEPES, 3 mM EGTA, and 10 mM TEA Cl.

Recordings of voltage gated channel activation and action potentials were measured and analyzed using pClamp software (Axon Instruments). Under current-clamp conditions, each patched cell was injected with 2 nA of current over 2 ms to stimulate an action potential, while the change in membrane potential was recorded. Under voltage clamp conditions, the membrane potential was stepped from a holding potential of −60 mV to 90 mV by steps of 10 mV, while channel currents were recorded. The family of current recordings were analyzed for the peak transient sodium channel currents and steady-state potassium channel currents and used to create a current-voltage relationship.

Immunocytochemistry:

Dissociated DRG cells in culture were fixed using 4% paraformaldehyde in 1 M phosphate buffer saline (PBS) for 60 minutes at room temperature (RT). Following fixation, the cells were rinsed three times with 1 M PBS and blocked with 4% normal goat serum in 0.1% Triton-X PBS for 30 minutes at RT. They were then incubated with antibodies to DRG marker Calcitonin gene related protein (CGRP; Chemicon, Temecula, Calif.) and several neurofilament (NF) markers: SMI-31 (specific for phosphorylated NF—H; Sternberger Monoclonal Incorporated); RMO-254 (specific for phosphorylated NF-M; a generous gift from Virginia M.-Y. Lee); and NF-200 (clone N52, Sigma). Each primary antibody was labeled with goat anti-mouse or rabbit IgG conjugated to Alexa 488 (Molecular Probes, Eugene, Oreg.) for 60 minutes at RT. Fluorescence microscopy was performed on a Nikon TE300 inverted microscope with a Cooke Sensicam digital camera.

Mechanical Elongation:

DRG axons were stretch-grown within a custom designed axon expansion chamber, which serves as tissue culture support and housing consisting of a sealed enclosure with gas exchange port, removable axon stretching frame, and connecting rods to apply displacements (Smith et al., 2001, Tissue Eng 7:131-139; Pfister et al., 2004, J Neurosci 24:7978-7983). The entire apparatus was sterilized prior to plating by a regular water-steam autoclave (Tuttnauer 2450M, Hauggauge, N.J.). This device arranges two adjoining ACLAR® membranes on which neural cells are cultured. Axons, growing in culture, readily bridged the interface between the two adjoining substrates and integrated with neurons on either side, spanning an approximately 100 µm gap. These bridged axons were then stretch-grown by displacing the two integrated populations of neurons apart in a stepwise fashion, using an automated micro stepper motor and controller system (Servo Systems, Montville, N.J.) according to an optimized stretch-growth paradigm previously described in detail (Smith et al., 2001, Tissue Eng 7:131-139; Pfister et al., 2004, J Neurosci 24:7978-7983)) and summarized below.

Elongator ACLAR® substrates were coated with type I collagen prior to DRG plating. ACLAR® was washed with laboratory soap, treated in 1M NaOH for 24 hours, and then sterilized in 100% ethanol for 10 minutes. ACLAR® substrates were attached to the stretching frame using medical grade RTV silicone (NuSil, Carpenteria, Calif.) and allowed to cure for a minimum of two days. Culture surfaces were then treated with 10 µg/mL poly-L-lysine for 2 hours then removed and allowed to dry for one hour before rinsing three times with sterile water. Type 1 rat-tail collagen (Becton Dickinson) as supplied was spread over the surface (10-20 µL per $cm^2$) and polymerized by exposure to ammonia vapors for 2 minutes. The collagen was then allowed to dry completely in the cell culture hood before plating cells. The hydrophobic collagen surface allows for cells to be plated within any desired arrangement by applying the cell suspension in a defined puddle.

Dissociated DRG neurons were plated on each of the two adjacent substrates within the elongation chamber and given 14 days for axons to develop in culture and span the dividing region (~100 µm) between the two membranes. Axon stretch-growth was initiated at a rate of 0.25 mm/day, and gradually escalated to a rate of 1 mm/day to reach a total length of at least about 1 cm.

The results of the experiments presented in example 8 are now described.

DRG were obtained from eighteen patients, including 14 live patients who underwent elective C2 ganglionectomy and 4 organ donors. The mean age for the elective surgery group was 42.6 and 23.8 for the donor group. The mean age for both groups combined was 38.4. The sex ratio was equal (9M:9F) for the combined group. See Table 1.

TABLE 1

|  | Live Patients (N = 14) | Donor Patients (N = 4) |
|---|---|---|
| Mean Age (years) | 42.6 (Range: 26-57) | 23.8 (Range: 2-52 yrs) 38.4 (Range 2 to 57) |
| Sex (M:F) | 5M:9F | 4M:0F 9M:9F |

The purified human DRG neurons harvested from both live and donor patients tolerated culture well in either the elongation apparatus or in collagen-coated 35 mm dishes. Within seven days following plating, an extensive network of axons had developed to interconnect neural cell bodies. Neurons cultured in 35 mm dishes consistently survived for more than three months, identified by both neuronal morphology and immunoreactivity to various neuron markers (FIGS. 10A-10D). Notably, the robust axon integration and viability of these neurons even after three months in culture suggests that much longer survival could be achieved. However, this survival was dependent on mitotic inhibitors in the culture media to prevent non-neuronal cell proliferation.

Overall, with the consistently robust survival and electrophysiologic behavior of isolated DRG from both organ donors and living patients, overt differences between groups was not observed. Likewise, the age of the organ donor or patient did not appear to have an effect on DRG neuron viability in culture, including neurons isolated from the only child in the study and from the oldest adult.

Figures 11A, 11B:
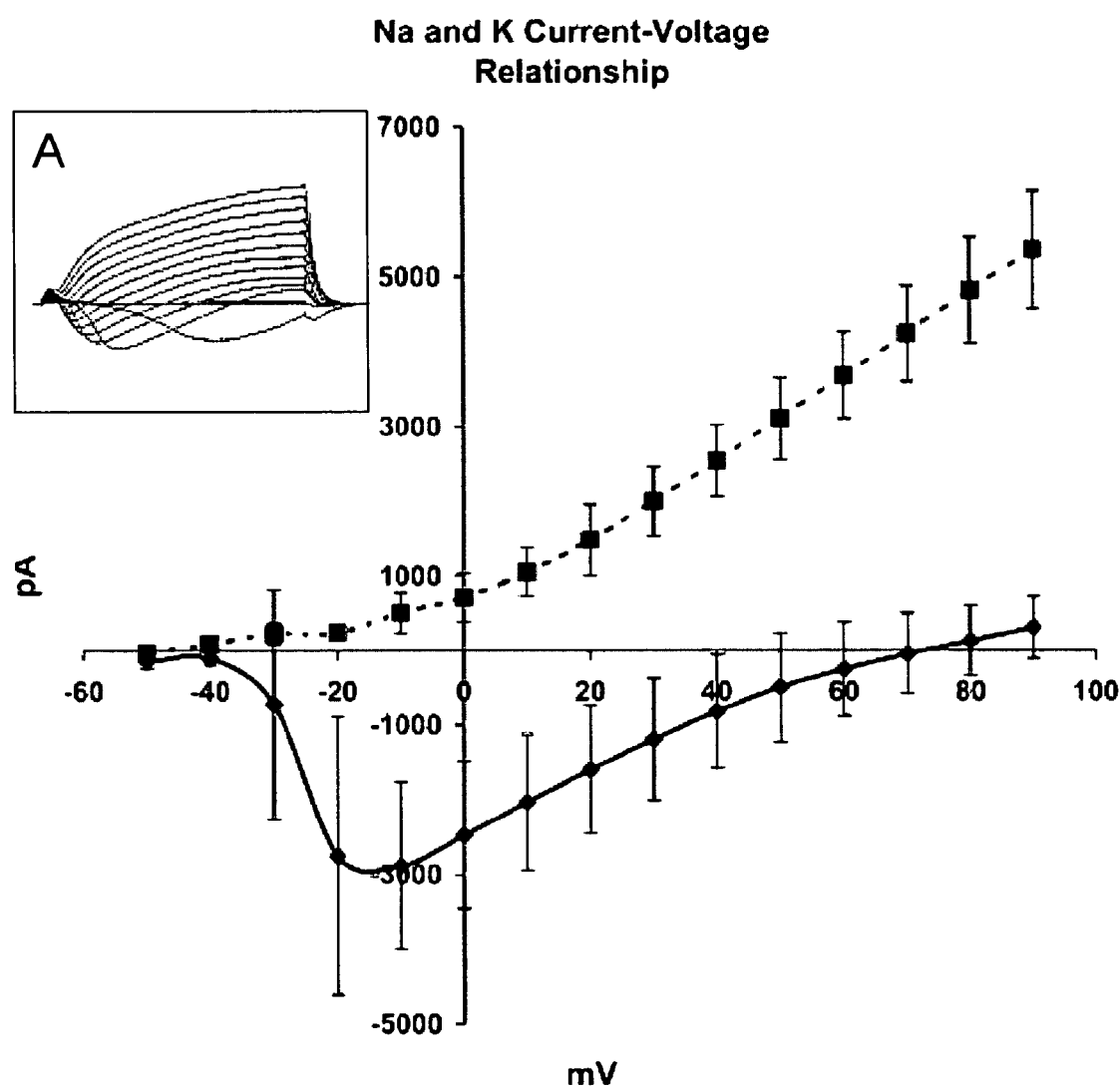
FIGS. 11A and 11B, depicts data from whole-cell patch clamping.

The electrophysiological function of the human DRG neurons was assessed using the whole cell variant of the patch clamp technique to assess whether the membrane properties of the cultured human DRG neurons maintained excitability in their in vitro culture environment. Isolated neurons were current-clamped, and a ramp of depolarizing current used to generate action potentials. After cells were successfully patched, for whole cell recording, the resting membrane potential was measured. The median resting potential was −43 mV. Cells were switched to current-clamp mode and stimulated with a 2 nA current injection. Each cell examined was able to generate an action potential (FIG. 11A). No irregularities in the wave forms were noted. In addition, the activation kinetics of the sodium and potassium channels was explored using a voltage-clamp protocol. From a holding potential of −60 mV, neurons were stimulated using a membrane potential step protocol to activate sodium and potassium channels. Peak currents were analyzed to create a current-voltage relationship (FIG. 11B). In all DRGs recorded, no abnormalities were found in the activation kinetics of either the sodium or potassium channels. Thus, these data demonstrate normal sodium and potassium channel behavior.

Figure 12:
FIG. 12 is an image of elongated human DRG axons, engineered from human neurons obtained from a live patient. Axons were stretched at a mechanical tension rate of 0.5 mm/day. Human DRG were immunostained with a neurofilament specific antibody (SMI-31, 1:200) and identified with secondary antibody Alexa Fluor-488 (1:200).

DRG neurons were also placed under an elongation paradigm of continuous mechanical tension previously described (Smith et al., 2001, Tissue Eng 7:131-139). FIG. 12 depicts representative axons from this trial, with the axons stained with SMI-31, an antibody to heavy chain neurofilament 200 kD. The cells were observed to tolerate the continuous stress and elongated to a length of at least 10 mm. Large fascicles 1 cm long spanning two populations could be easily visualized by eye, and these fascicles were identified as axons by fluorescent immunoreactivity to antibodies targeting neurofilament proteins.

Example 9

Tissue-Engineered Nerve Constructs Implanted in Injured Rat Spinal Cords

The materials and methods used in this example are now described.

Embryonic Dorsal Root Ganglion Cell Isolation:

Whole DRG explants were used in the system since whole DRG cultures allow for very high plating densities and lead to much larger axon fascicles during mechanical elongation growth. DRGs were isolated from E15 rat embryos. DRG cultures were maintained in complete growth medium consisting of Neural Basal Medium (INVITROGEN™) supplemented with B27 (INVITROGEN™), 1% FBS (Hyclone) and 1 mM L-Glutamine (INVITROGEN™), 2.5 g/l glucose, and 10 µg/ml 2.5S nerve growth factor (INVITROGEN™).

Axonal Elongation Apparatus:

Axons were stretch-grown in elongation devices specially designed and built for these studies (Smith et al., 2001, Tissue Eng 7:131-139). The axon elongation device consists of a custom-built, autoclavable TEFLON® box with a gas exchange port and removable top. The device was created to gradually separate two adjoining substrates on which neural cells are cultured. The adjoining substrates were designed such that axons growing in culture can easily grow across the interface of the overlapping substrates. The bottom substrate (19 µm thick), upon which a stationary population of neurons is cultured, is made of optically transparent ACLAR® 33C film (Structure Probe, West Chester, Pa.) and covers the entire bottom of the elongation device. An overlapping ACLAR® substrate, the "towing" substrate (51 µm thick and polished to approximately 10 µm thick), is placed on top of the bottom ACLAR® substrate and serves to "tow" the moving population of cells. Once the neurons and their axons have matured and integrated across the interface between the bottom and towing substrates, the two substrates are separated using a microstepper motor system comprising a linear table (Servo Systems, Inc., Montville N.J.) and a microstepper motor (Applied Motion Products, Watsonville, Calif.). Control of the movement is computer programmed using a motor indexer/driver (Applied Motion Products, Watsonville, Calif.) and results in two populations of cell bodies connected together via elongated fascicular axon tracts.

Elongation Device Preparation, Plating, and Maintenance:

The ACLAR® surfaces of the elongator were coated with poly-L-lysine and type I collagen prior to DRG culture. Treating ACLAR® in 1M NaOH for 24-48 hours was found to increase the hydrophilicity of the surface and facilitate the even spread of collagen. ACLAR® was sterilized in 100% EtOH for 10 minutes before coating with collagen. The ACLAR® substrates were attached to the elongator framework using medical grade RTV silicone (NuSil) that is non-toxic to cells when fully cured. Twenty-four hours after assembly, the ACLAR® surfaces were treated with 10 µg/ml poly-L-lysine, followed by a coating of type 1 rat-tail collagen (Becton Dickinson). Collagen as supplied was spread over the surface (10-20 µl per cm$^2$) and polymerized by exposure to ammonia vapors for 2 minutes. The collagen was then allowed to dry completely in the cell culture hood before plating the cells. The hydrophobic collagen surface allowed for cells to be plated within any desired arrangement by applying the cell suspension in a puddle and allowing the cells to attach for about 2-4 hours before the chamber is filled with media. Five hundred (500) µl of whole embryonic DRG explants in complete medium, obtained from 8-10 pups, were plated along the elongator substrate interface. After the cells attached to the surface, DRG cultures were treated immediately with mitotic inhibitors (MI#1: 5 µM cytosine arabinoside (Sigma), 20 µM 5-fluoro-2'-deoxyuridine (Sigma), and 20 µM uridine (Sigma)). After two days, the medium was exchanged with complete medium plus the mitotic inhibitors (MI#2: 20 µM 5-fluoro-2'-deoxyuridine, and 20 µM uridine) for three days, and changed weekly thereafter.

Cell Tracking following Transplantation:

Two techniques were used to assist in differentiating graft cells from host cells. In one technique, elongated axons and their neuronal cell bodies, the transplant nerve grafts, were labeled with biotinylated dextran amines (BDA; Molecular Probes, Eugene, Oreg.; 10% wt/vol solution) (Nelms et al., 2002, Exp Neurol 174:72-80) at day 12 in vitro (DIV 12) just before transplantation. In another technique, elongated axons and their neuronal cell bodies were labeled with Vybrant™ CFDA SE Cell Tracer Kit (Molecular Probes) at DIV 12 just before transplantation.

Figure 13:
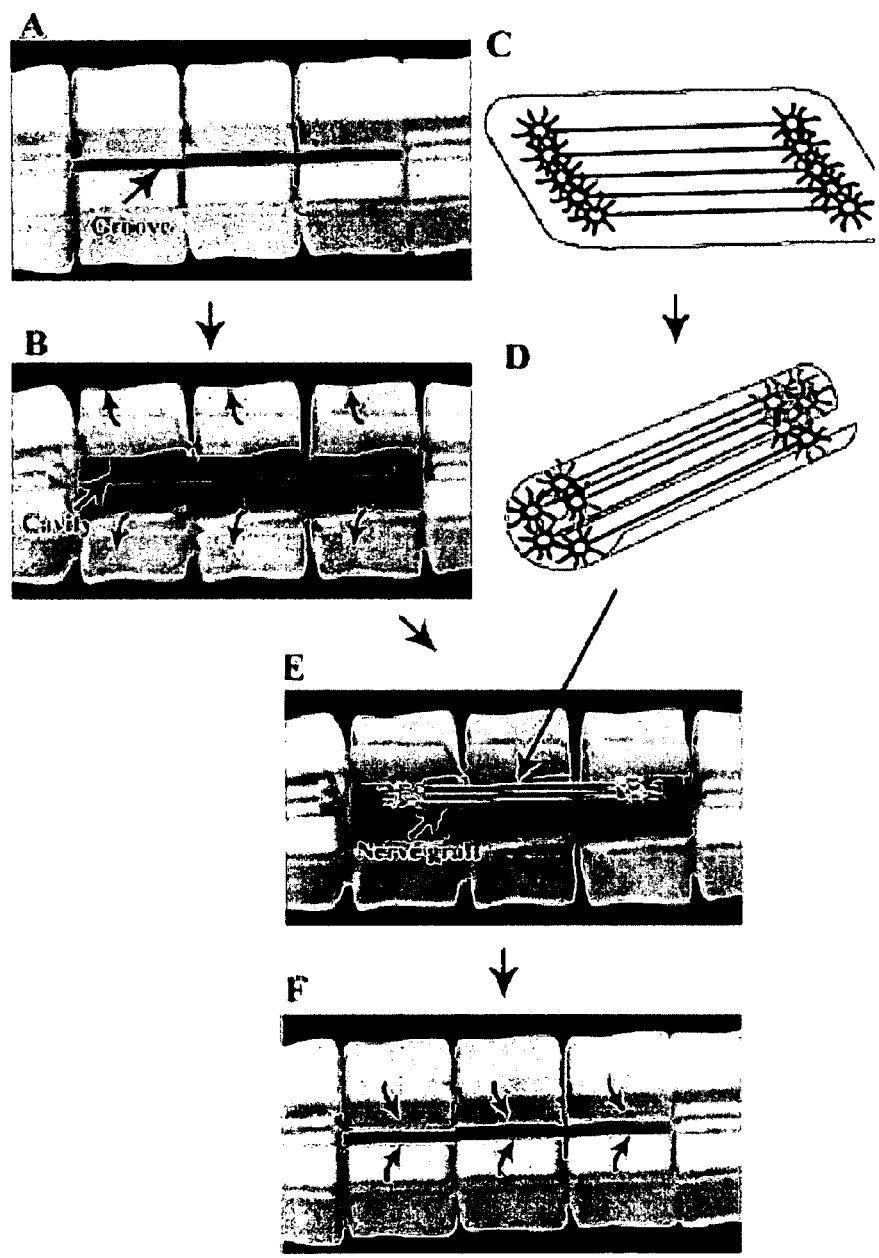
FIG. 13, comprising

Spinal Cord Injury Model:

Adult female Sprague-Dawley rats (n=15) weighing 225-250 grams were used as the spinal cord injury (SCI) model. Rats were anesthetized with 40 mg/kg pentobarbitol injected i.p. Operative procedure was performed using standard aseptic technique. Under a surgical microscope (Wild Heerbrugg, Heerbrugg, Switzerland), an open-door expansive laminoplasty was made at the 9th-to-11 th thoracic (Th9-Th11) spinal vertebrae (FIGS. 13A and 13C). After incising the dura, a longitudinal cut along the dorsal central vein of the cord was performed using a 30 G needle and microscissors. This was followed by aspiration of the spinal cord in this region, resulting in a 1 cm-long hemisection. The cavity was filled with GELFOAM® (Pharmacia & Upjohn, Kalamazoo, Mich.) for hemostasis and to avoid a collapse of the cavity. The dura was closed with 10-0 monofilament nylon (Ethicon). A piece of TEFLON® tape was placed on the dura, and laminoplasty was made using GELFOAM® and VETBOND® (3M, St. Paul, Minn.) to prevent connective tissue from invading the spinal column and compressing the spinal cord. The muscle and skin were closed in layers.

All surgical procedures and post-operative observations were done on a heating pad. Cefazolin (30 mg/kg, i.m.; APP, Inc., Los Angeles, Calif.) was injected for 7 days after injury to prevent against infection. Manual bladder expression was performed twice per day until reflex bladder emptying was established. Three days before the transplantation, an Alzet osmotic pump (Cupertino, Calif.), filled with an immunosuppressive drug (Cyclosporin A, 10 mg/kg/day), was intraperitoneally implanted under general anesthesia.

Transplant of DRG Nerve Construct into an Injured Spinal Cord:

To protect the nerve graft from damage during the operation and to assist the potential integration between graft and host, a collagen-based hydrogel impregnated with nerve growth factor (NGF) was used. The collagen-based hydrogel was a mixture of 10 µl of 100 µg/ml 2.5S NGF (INVITROGEN™), 10 µl of 1 N NaOH, 180 µl of tissue culture grade $H_2O$, 800 µl of rat type I collagen (3.67 g/ml; BD), and 100 µl of 10× media consisting of 10×MEM (Sigma), 59.58 g/l HEPES (Sigma), and 22.0 g/l $NaCHO_3$ (Sigma). Immediately after axonal elongation at DIV 12, the nerve grafts were encased with the hydrogel (FIG. 13C), peeled off from the bottom substrate, and held with a micro-spatula (FIG. 13D). Then, the hydrogel-encased nerve graft (n=10) or hydrogel alone (n=5) was transferred into the cavity), 10 days following the initial SCI. After re-opening the initial wound, the GELFOAM® was evacuated without any further spinal cord damage. The nerve construct was transferred into the cavity (FIG. 13E. The wound was closed with a Gelforam and Vetbond complex (FIG. 13F) and the animals were postoperatively treated as above.

Tissue Processing for Immunohistochemistry:

Animals were anesthetized with lethal injections of sodium pentobarbital (200 mg/kg, i.p.), and were perfused transcardially with heparinized saline and 4% paraformaldehyde in 1 M phosphate buffer saline (PBS). The spinal cords were removed and postfixed in 4% paraformaldehyde overnight at 4° C. Two-centimeter blocks of the thoracic region of the cords, including injury epicenters, were immersed in 25% sucrose in 1 M PBS and kept at 4° C. until use. Serial longitudinal sections (20 µm) were cut on a cryostat (Leica, Malvern, Pa.), and mounted on poly-L-lysine coated slides. The sections were used for immunohistochemistry (IHC).

Immunohistochemistry:

IHC was performed on 20-µm mounted sections employing the following antibodies: rabbit anti-neurofilament 200 (NF200; 1:200; Sigma), specific for neurofilament heavy-chain or anti-neurofilament (SMI-31 and SMI-32; Sternberger Monoclonals, Lutherville, Md.), specific for both phosphorylated and non-phosphorylated neurofilament heavy-chain; rabbit anti-calcitonin gene related peptide (CGRP; 1:1000; Sigma) specific for DRGs and primary afferent sensory neurons; mouse anti-synaptophysin (1:200; Sigma), specific for synaptic proteins; and Alexa 488-conjugated mouse anti-BDA (1:200; Molecular Probes) for detecting the transplanted nerve grafts. Briefly, sections were treated with 3% $H_2O_2$ in methanol to block endogenous peroxidase activity, blocked with 4% normal horse serum for 30 minutes at RT, and permeabilized with 0.1% Triton X-100 for 20 minutes. Sections were incubated with the primary antibodies overnight at 4° C. After rinsing with PBS, the sections were incubated with Alexa 350-conjugated anti-mouse IgG, Alexa 488-conjugated anti-BDA (Molecular Probes), and Alexa 594-conjugated anti-rabbit IgG (Molecular Probes) for 60 minutes at RT. Fluorescence microscopy was performed on a Nikon Eclipse E600 with a SPOT RT digital camera (Diagnostic Instruments Inc, Sterling Heights, Mich.) and a Radiance 2000 confocal microscope (Bio-Rad, Hercules, Calif.). In addition, transplants were treated with cell tracking methods to differentiate graft from host tissue (see above). Each animal was subjected to extensive analysis to assess the survival of grafts, as well as potential integration with host tissue.

The results of the experiments presented in example 9 are now described.

In the present study, it was a big challenge to prevent the collapse of the SCI cavities from subcutaneous connective tissue compression. After a process of trial and error, an expansive open-door laminoplasty method was developed. This new method prevented collapse of SCI cavities as well as post-operative spinal deformation after expansive laminectomy that removed all of three laminas without plasty.

A unique hydrogel-encased transferring method was developed (FIG. 13) to transfer the culture cells with elongated axons, in vitro, into the SCI cavity, in vivo. Using this transferring method, the living nerve cells and axons are protected by a collagen-based hydrogel and can be safely transferred into an SCI lesion. In this example, the nerve constructs were encased with collagen-based hydrogel and treated with nerve growth factor to assist in the survival of the graft and in the integration between graft and host. This is the first known example of the transfer of hydrogel-encased living networked neurons and axons into SCI lesions.

Figure 14:
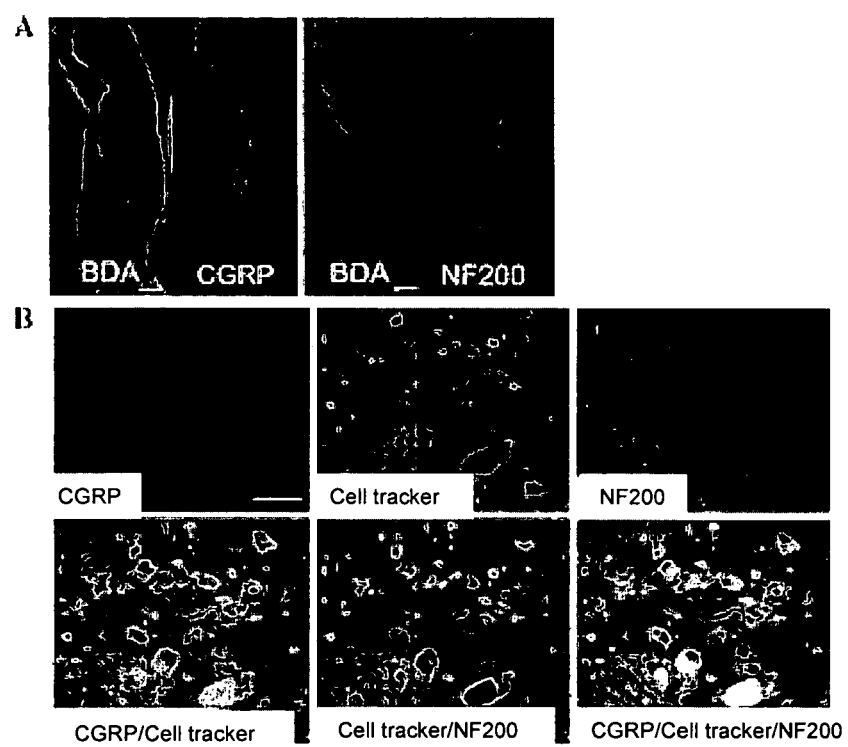
FIG. 14, comprising

At one month following transplant, the survival of the transplanted tissue was evaluated using BDA and CGRP (or NF200) immunohistochemistry. Hydrogel-encased DRGs and axons, strongly double-labeled with BDA and CGRP or NF, had clearly survived. FIG. 14A. The DRGs and axons were sandwiched between two layers of collagen-based hydrogel, which had not disappeared at one month post-transplantation. DRG clusters, triple-labeled with CGRP, Cell Tracker, and NF200, were also observed in the edge of the SCI cavity (FIG. 14B). Axonal outgrowth from DRG clusters, triple-labeled with anti-CGRP, NF200 antibodies, and CellTracker, was observed in the edge of the SCI cavity where the Gelfoam still existed. Since there are no CGRP containing neuronal cell bodies in the normal spinal cord, this marker provided firm evidence of survival of the transplanted DRG neurons.

Figure 15:
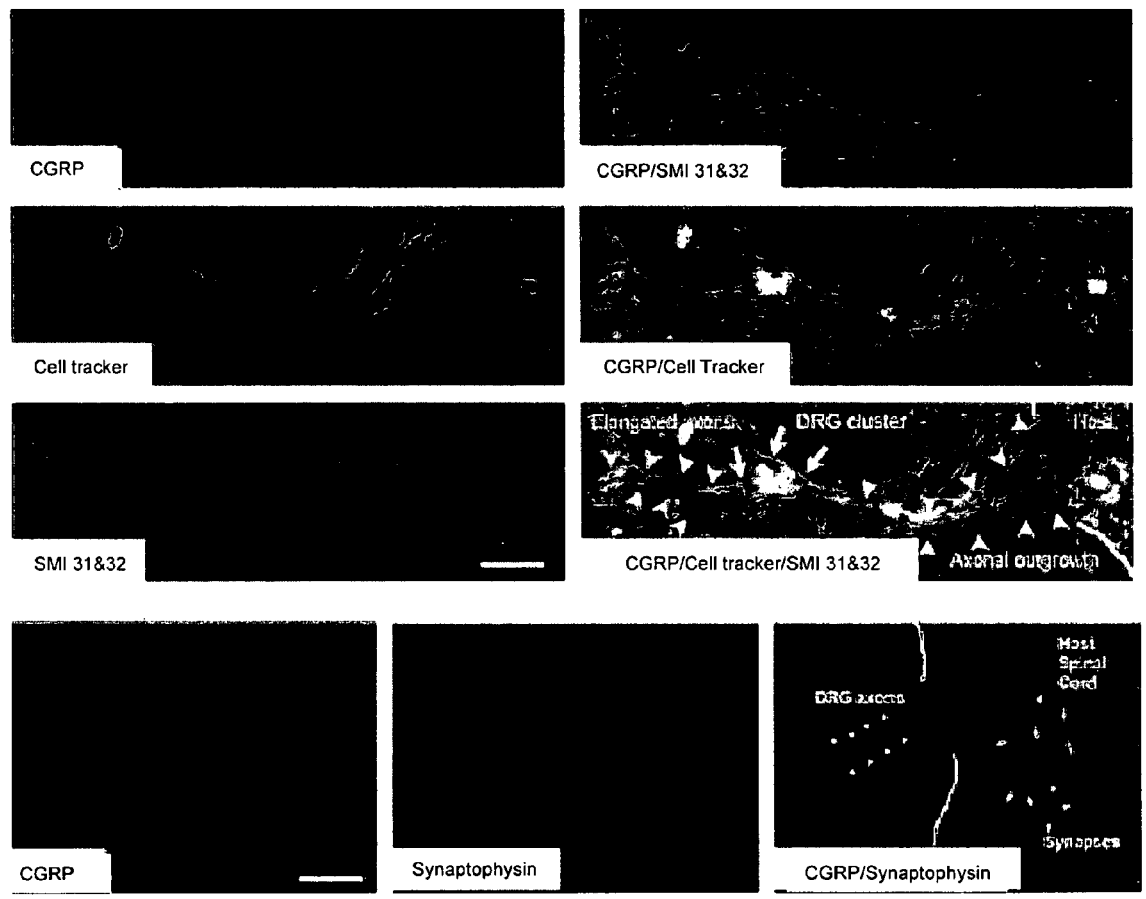
FIG. 15, comprising

Triple-labeling with anti-CGRP, SMI 31 &32 antibodies and cell tracker illustrated that there was axonal outgrowth from the DRG neurons (FIG. 15). These axons extended through the collagen barrier, penetrating into the host tissue. Positive staining by anti-synaptophysin antibody suggested the presence of synaptic, in association with axons staining for CGRP that extended into the host tissue.

Example 10

Tissue-Engineered Nerve Constructs Implanted in Injured Rat Sciatic Nerves

The materials and methods used in this example are now described.

Nerve Construct:

In order to distinguish host nerves from nerves in the nerve construct, transgenic animals were prepared. One colony consists of green fluorescent protein transgenic (GFP-Tg) rats and another colony consists of alkaline phosphatase (AP+) transgenic rats. GFP-positive DRG axons were successfully elongated and appeared to respond to mechanical stretch in the same fashion as axons from non-transgenic rats.

The GFP-Tg rats were used to create GFP+ nervous tissue constructs to be implanted into AP+ rats. The nerve construct was made using elongated embryonic GFP+DRGs in a collagen matrix. This composition was then inserted into a polyglycolic acid mesh tube (Neurotube, Synovis MCA, Birmingham, Ala.) to serve as a sheath. The nerve construct was then transplanted into the site of the sciatic nerve lesion. The recipient rats did not receive any immunosuppressive therapy.

Sciatic Nerve Mode and Transplantation:

Experimental subjects were 30 male Sprague Dawley rats with a mass between 300 g and 400 g. The institutional animal care and use committee (IACUC) of the University of Pennsylvania approved all surgical procedures.

Animals were anesthetized by intraperitoneal injections of sodium pentobarbital (60 mg/kg). Additional anesthetic was supplemented as needed to preserve an insensate anesthesia plane. Core body temperature was maintained at 37° C. during anesthesia using a heating pad. The left sciatic nerve was exposed in all animals through a transverse incision of the gluteus maximus. The nerve was debrided from surrounding fascia, 1 cm was measured, and the epineurium was marked with a felt-tip marker. The measured segment was removed by transecting the nerve with a sharp scalpel in all but sham animals. After transection, the proximal and distal stumps of the nerve retracted slightly to extend the gap to approximately 1.3 cm.

Rats were divided into four experimental groups based on the repair strategies that were employed after excision of a 1 cm sciatic nerve segment: 1) 9 rats were transplanted with the living nerve construct, 2) 10 rats were repaired using an autologous graft with reverse orientation, 3) 6 rats were not repaired after transection, and 4) 6 rats were subjected to a sham surgery, exposing the sciatic nerve without transection.

Functional Recovery Assessment:

The angle board challenge, a walking track analysis as a Sciatic Function Index (SFI) and hind limb flexion were used to evaluate neurologic motor and sensory recovery after nerve injury.

The angle board challenge measures the ability of rats to stand on an incline plane without slipping. Prior to nerve injury, the greatest angle at which animals could avoid slipping was an incline of 35° (n=24). This angle was used as a minimum threshold to demonstrate full recovery.

The results of the experiments presented in example 10 are now described.

Functional recovery was tested using the angle board challenge. A blinded examination of animals at 4 months after injury demonstrated that none of the non-repaired animals could reach the minimum threshold. In contrast, 22% of animals that had been repaired with a reverse autologous graft (n=10) and 33% of animals with the living nervous tissue construct (n=9) successfully reached the minimum threshold. This preliminary assessment demonstrated motor recovery in animals receiving the nervous tissue to at least to the same extent as animals receiving the conventional 'gold standard' autologous graft. These data indicate that the nerve construct ameliorated, at least in part, the sciatic nerve lesion.

Figure 16:
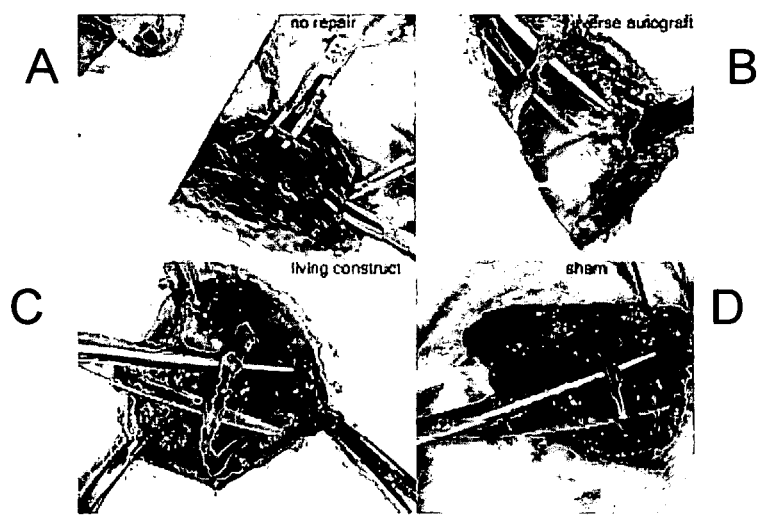
FIG. 16, comprising

At 4 months after injury, the sciatic nerves were exposed for gross examination and extracellular electrophysiological recordings. All animals transplanted with either the nerve construct (n=9; FIG. 16C) or reverse autograft (n=10; FIG. 16B) had relatively normal appearing nerves across the transected region. For the nerve construct, the PGA tube had been completely absorbed by this post-transplantation time point. In animals with no repair of the transected nerve, none of the nerves were patent, and the proximal nerve stump was adherent to local soft tissue (n=6; FIG. 16A). FIG. 16D depicts the sciatic nerve in a sham-operated rat.

Figure 17:
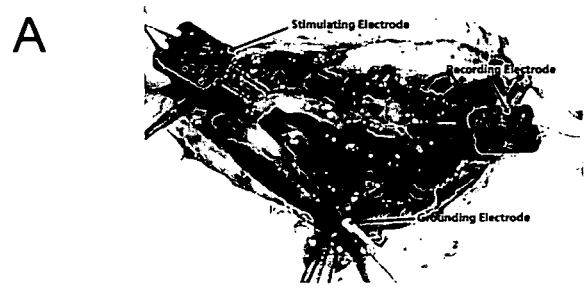
FIG. 17, comprising
Figure 17:
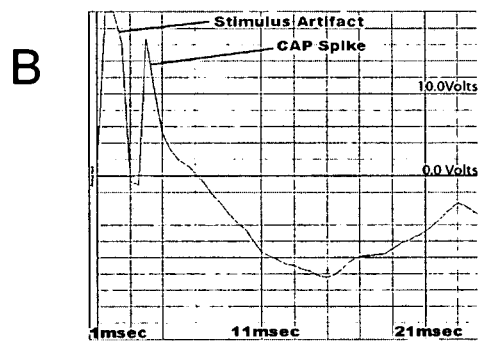
Figure 17:
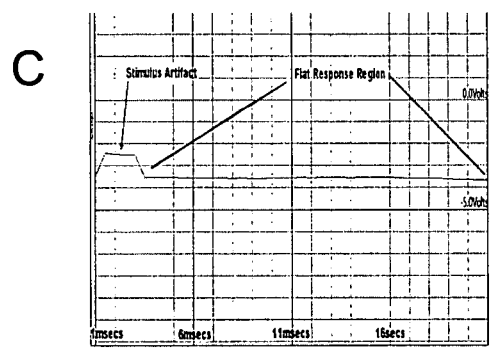

An important measure of recovery after nerve injury is the capacity of regenerated axon tracts to conduct action potentials. Therefore, compound action potentials were stimulated and recorded with hooked electrodes contacting the epineurium directly (FIG. 17A). Rats were tested for electrophysiology four months following injury and nerve repair. Compound action potentials were elicited in all rats that had been repaired with either the living nervous tissue construct (n=9; FIG. 17B) or a reverse allograft (n=10). Rats that had the sciatic nerve injury but were not repaired were stimulated in an identical fashion. However, no compound action potentials were found to traverse the nerve lesion (n=6; FIG. 17C).

Figure 18:
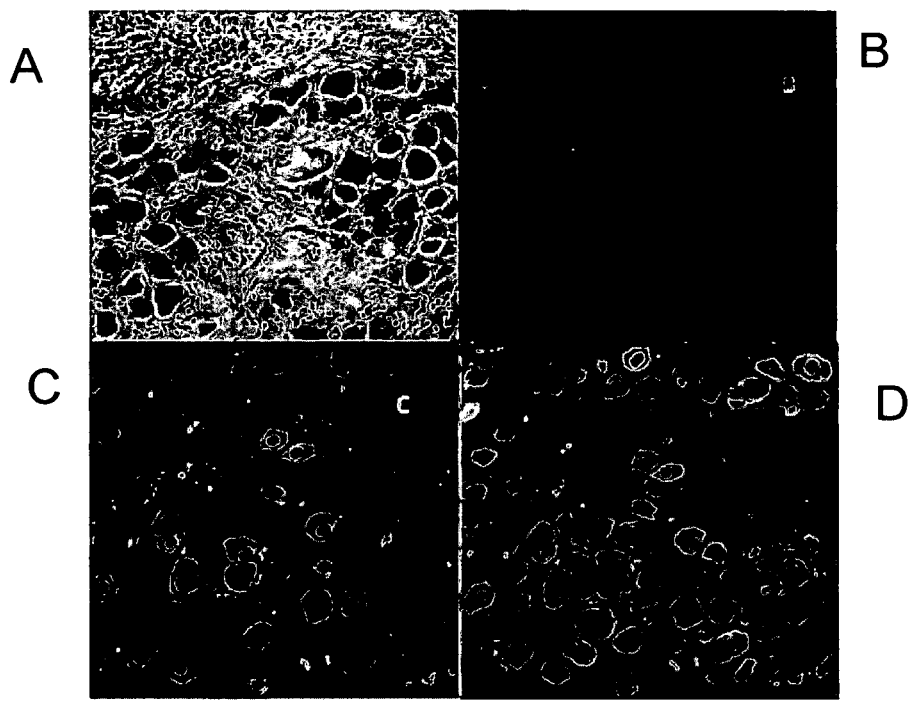
FIG. 18, comprising
Figure 19:
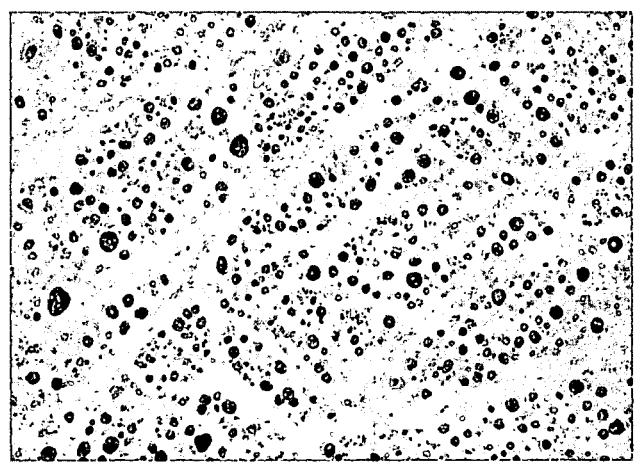
FIG. 19 is an image of an axial section of a transplanted injury region 4 months after transplantation. The section is myelin basic protein stained. There are numerous myelinated axons in the middle of the graft site.

Four months after transplantation with the transplanted nervous tissue construct (n=9), large clusters of DRG neurons immunoreactive to antibodies specific for neurofilament proteins (NF200) and CGRP were observed at each end of the transplanted region and a high density of axons throughout the middle (FIG. 18). Since neurons are not naturally found in the nerve, this observation conclusively demonstrated that transplanted DRG neurons survived within a developing axonal framework for 4 months. Robust myelination was also observed in axial sections of the transplanted injury region (FIG. 19). Surprisingly, despite the absence of immunosuppression, there was no evidence of host rejection of the construct, such as infiltrating macrophages or lymphocytes.

Figure 20:
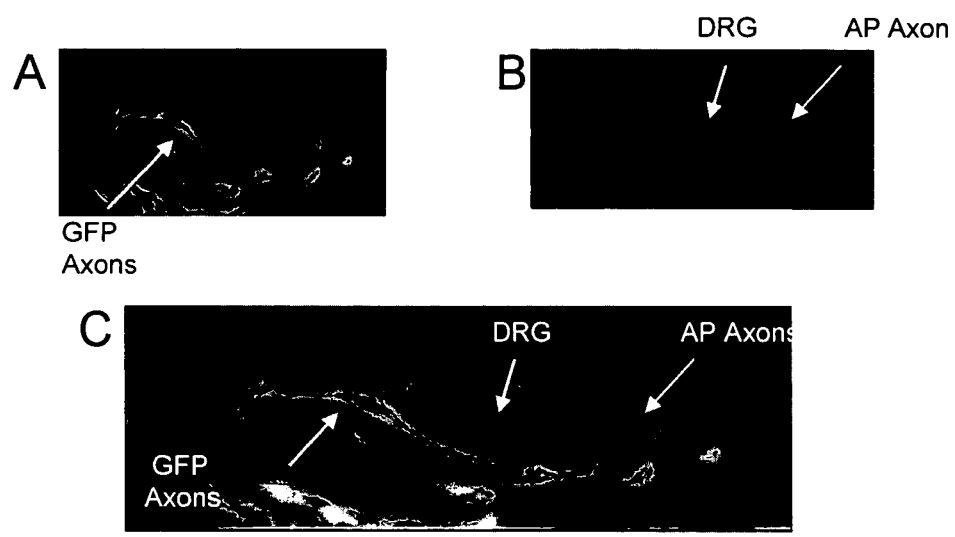
FIG. 20, comprising

To discern the host axons from axons of graft origin in the middle of the grafted region of the nerve, in a separate experiment, five 1.3 cm long constructs, derived from GFP+ Tg rats DRG, were transplanted into AP+ Tg rats (n=5) that had received a 1.3 cm sciatic nerve injury. The animals were allowed to survive for different lengths of time: 1 mo (n=2), 2 mo (n=1), 3 mo (n=1) and 4 mo (n=1). Following euthanasia, the nerves were fixed and sectioned longitudinally, including the 1.3 cm transplantation site, as well as 1 cm nerve segments proximal and distal to the repair site. While green fluorescence could be detected in the sections without staining, the signal was enhanced using antibodies against GFP and double stained with antibodies against neurofilament (NF) protein. In all animals, dense survival of axons double labeled with GFP and NF was observed, demonstrating that many axons in the repaired region were from the transplanted elongated nerve construct. Surprisingly, there was robust and comprehensive integration of these GFP+ axons with host axons (lacking GFP staining). FIG. 20 depicts an representative image of GFP+ axons and host axons appeared intertwined together. Without being bound by theory, it is believed that the living elongated DRG cultures provided a persistent labeled pathway for outgrowth and regeneration of host axons. In addition, GFP+ graft axons growing both proximally and distally 0.5 cm into the host nerve were observed. Accordingly, the axons growing out of the transplanted construct may extend into the periphery, potentially extending the labeled pathway, which would further assist host axon regeneration.

What is claimed is:

1. A composition comprising:
a plurality of integrated neuronal cells, and
a biocompatible matrix,
wherein said plurality of integrated neuronal cells comprises two populations of cell bodies of mechanically elongated neurons, said two populations connected to each other by elongated fascicular axon tracts, and
wherein said mechanically elongated neurons are coated in said biocompatible matrix to form a sheet of matrix-coated integrated neuronal cells, such that said biocompatible matrix physically supports said mechanically elongated neurons and prevents damage to said axon tracts and wherein said sheet is rolled into a cylindrical shape.

2. The composition of claim 1, wherein the mechanically elongated neurons are selected from the group consisting of a dorsal root ganglion (DRG) neuron, a sympathetic ganglion neuron, and a cortical neuron.

3. The composition of claim 2, wherein the neurons are human neurons.

4. The composition of claim 1, wherein the axons of the mechanically elongated neurons are elongated to at least 1 centimeter.

5. The composition of claim 4, wherein the axons are elongated to at least 5 centimeters.

6. The composition of claim 1, wherein the biocompatible matrix comprises a collagen hydrogel.

7. The composition of claim 1, wherein the biocompatible matrix further comprises one or more neurotrophic factors.

8. The composition of claim 7, wherein the one or more neurotrophic factors is selected from the group consisting of nerve growth factor (NGF), brain derived neurotrophic factor (BDNF), neurotrophin 3 (NT-3), neurotrophin 4/5 (NT-4/5), neurotrophin 6 (NT-6), neurotrophin 7 (NT-7), ciliary neurotrophic factor (CNTF), neurturin (NTN), persephin, artemin, basic fibroblastic growth factor (bFGF), glial-cell-derived neurotrophic factor (GDNF), purpurin and a synthetic neurotrophin.

9. The composition of claim 8, wherein the one or more neurotrophic factor is nerve growth factor.

10. The composition of claim 1, further comprising a sheath, wherein said sheath at least partially enfolds said composition.

11. A method of treating a nerve lesion in a subject, the method comprising administering to the subject a therapeutically effective amount of a composition comprising a plurality of integrated neuronal cells, and
a biocompatible matrix,
wherein said plurality of integrated neuronal cells comprises two populations of cell bodies of mechanically elongated neurons, said two populations connected to each other by elongated fascicular axon tracts, and
wherein said mechanically elongated neurons are coated in said biocompatible matrix to form a sheet of matrix-coated integrated neuronal cells, such that said biocompatible matrix physically supports said mechanically elongated neurons and prevents damage to said axon tracts and wherein said sheet is rolled into a cylindrical shape.

12. The method of claim 11, wherein the mechanically elongated neurons are synapsed prior to administering the composition to the subject.

13. The method of claim 11, wherein the mechanically elongated neurons are selected from the group consisting of a DRG neuron, a sympathetic ganglion neuron, and a cortical neuron.

14. The method of claim 13, wherein the neurons are human neurons.

15. The method of claim 11, wherein the mechanically elongated neurons are elongated to at least 1 centimeter.

16. The method of claim 11, wherein the mechanically elongated neurons are is elongated to at least 5 centimeters.

17. The method of claim 11, wherein the biocompatible matrix comprises a collagen hydrogel.

18. The method of claim 11, wherein the biocompatible matrix further comprises one or more neurotrophic factors.

19. The method of claim 18, wherein the one or more neurotrophic factors is selected from the group consisting of nerve growth factor (NGF), brain derived neurotrophic factor (BDNF), neurotrophin 3 (NT-3), neurotrophin 4/5 (NT-4/5), neurotrophin 6 (NT-6), neurotrophin 7 (NT-7), ciliary neurotrophic factor (CNTF), neurturin (NTN), persephin, artemin, basic fibroblastic growth factor (bFGF), glial-cell-derived neurotrophic factor (GDNF), purpurin and a synthetic neurotrophin.

20. The method of claim 19, wherein the one or more neurotrophic factor is nerve growth factor.

21. The method of claim 11, wherein the composition further comprises a sheath, wherein said sheath at least partially enfolds said composition.

22. The method of claim 11, wherein the nerve lesion is in the central nervous system of the subject.

23. The method of claim 22, wherein the nerve lesion is a spinal cord injury.

24. The method of claim 11, wherein the subject is a human.

* * * * *